United States Patent
Voronenko

(10) Patent No.: US 12,251,579 B2
(45) Date of Patent: Mar. 18, 2025

(54) MULTI-SENSOR GUIDED RADIATION THERAPY

(71) Applicant: RefleXion Medical, Inc., Hayward, CA (US)

(72) Inventor: Yevgen Voronenko, San Jose, CA (US)

(73) Assignee: RefleXion Medical, Inc., Hayward, CA (US)

( * ) Notice: Subject to any disclaimer, the term of this patent is extended or adjusted under 35 U.S.C. 154(b) by 109 days.

(21) Appl. No.: 18/163,176

(22) Filed: Feb. 1, 2023

(65) Prior Publication Data

US 2023/0256266 A1  Aug. 17, 2023

Related U.S. Application Data

(63) Continuation of application No. PCT/US2021/044405, filed on Aug. 3, 2021.

(Continued)

(51) Int. Cl.
*A61N 5/10* (2006.01)

(52) U.S. Cl.
CPC ......... *A61N 5/1067* (2013.01); *A61N 5/1039* (2013.01); *A61N 5/1081* (2013.01);
(Continued)

(58) Field of Classification Search
CPC .. A61N 5/1067; A61N 5/1039; A61N 5/1081; A61N 2005/1055;
(Continued)

(56) References Cited

U.S. PATENT DOCUMENTS

| | | |
|---|---|---|
| 3,794,840 A | 2/1974 | Scott |
| 5,015,851 A | 5/1991 | Singh et al. |

(Continued)

FOREIGN PATENT DOCUMENTS

| | | |
|---|---|---|
| CA | 1121072 A | 3/1982 |
| CN | 1681436 A | 10/2005 |

(Continued)

OTHER PUBLICATIONS

Bao, Q. et al. (2010). "Estimation of the minimum detectable activity of preclinical PET imaging systems with an analytical method," Med. Phys. 37:6070-6083.

(Continued)

*Primary Examiner* — Kiho Kim
(74) *Attorney, Agent, or Firm* — Cooley LLP

(57) ABSTRACT

Disclosed herein are methods for radiotherapy treatment planning and delivery that use sensor data from one or more target sensors. One variation of a radiotherapy treatment planning method comprises generating a sensor characterization image based on a sensor characterization probability density function (PDF) of a target sensor and calculating a set of firing filters that may be applied to sensor images generated from sensor data acquired during a radiation-delivery session. Additionally, a variation of a radiotherapy treatment planning method comprises generating multiple sensor characterization images based on multiple sensor characterization PDF of multiple target sensors and calculating multiple sets of firing filters for each of the multiple target sensors. The firing filters may be used with sensor images generated from target sensor data acquired from one or more target sensors during a radiation-delivery session to calculate a radiation fluence for delivering therapeutic radiation to a target region.

42 Claims, 12 Drawing Sheets

Related U.S. Application Data

(60) Provisional application No. 63/062,792, filed on Aug. 7, 2020.

(52) U.S. Cl.
CPC ............. *A61N 2005/1055* (2013.01); *A61N 2005/1059* (2013.01); *A61N 2005/1061* (2013.01); *A61N 2005/1074* (2013.01)

(58) Field of Classification Search
CPC .... A61N 2005/1059; A61N 2005/1061; A61N 2005/1074; A61N 5/1049; A61N 2005/1052; A61N 5/107
See application file for complete search history.

(56) References Cited

U.S. PATENT DOCUMENTS

| | | | |
|---|---|---|---|
| 5,394,452 A | 2/1995 | Swerdloff et al. |
| 5,548,627 A | 8/1996 | Swerdloff et al. |
| 5,661,773 A | 8/1997 | Swerdloff et al. |
| 5,724,400 A | 3/1998 | Swerdloff et al. |
| 5,813,985 A | 9/1998 | Carroll |
| 6,438,202 B1 | 8/2002 | Olivera et al. |
| 6,455,856 B1 | 9/2002 | Gagnon |
| 6,504,899 B2 | 1/2003 | Pugachev et al. |
| 6,700,949 B2 | 3/2004 | Susami et al. |
| 6,735,277 B2 | 5/2004 | McNutt et al. |
| 6,888,919 B2 | 5/2005 | Graf |
| 7,020,233 B1 | 3/2006 | Tybinkowski et al. |
| 7,085,347 B2 | 8/2006 | Mihara et al. |
| 7,177,386 B2 | 2/2007 | Mostafavi et al. |
| 7,191,100 B2 | 3/2007 | Mostafavi |
| 7,263,165 B2 | 8/2007 | Ghelmansarai |
| 7,265,356 B2 | 9/2007 | Pelizzari et al. |
| 7,302,033 B2 | 11/2007 | Carrano et al. |
| 7,302,038 B2 | 11/2007 | Mackie et al. |
| 7,356,112 B2 | 4/2008 | Brown et al. |
| 7,367,955 B2 | 5/2008 | Zhang et al. |
| 7,453,984 B2 | 11/2008 | Chen et al. |
| 7,469,035 B2 | 12/2008 | Keall et al. |
| 7,496,181 B2 | 2/2009 | Mazin et al. |
| 7,522,779 B2 | 4/2009 | Fu et al. |
| 7,620,444 B2 | 11/2009 | et al. |
| 7,623,623 B2 | 11/2009 | Raanes et al. |
| 7,649,981 B2 | 1/2010 | Seppi et al. |
| 7,711,087 B2 | 5/2010 | Mostafavi |
| 7,715,606 B2 | 5/2010 | Jeung et al. |
| 7,769,430 B2 | 8/2010 | Mostafavi |
| 7,778,691 B2 | 8/2010 | Zhang et al. |
| 7,783,335 B2 | 8/2010 | Le Corre |
| 7,820,989 B2 | 10/2010 | Sommer |
| 7,831,073 B2 | 11/2010 | Fu et al. |
| 7,869,562 B2 | 1/2011 | Khamene et al. |
| 7,869,862 B2 | 1/2011 | Seppi et al. |
| 7,885,371 B2 | 2/2011 | Thibault et al. |
| 7,906,770 B2 | 3/2011 | Otto |
| 7,945,021 B2 | 5/2011 | Shapiro et al. |
| 7,983,380 B2 | 7/2011 | Guertin et al. |
| 8,017,915 B2 | 9/2011 | Mazin |
| 8,060,177 B2 | 11/2011 | Hamill |
| 8,086,004 B2 | 12/2011 | Kuduvalli et al. |
| 8,093,568 B2 | 1/2012 | Mackie et al. |
| 8,148,703 B2 | 4/2012 | Sommer |
| 8,160,205 B2 | 4/2012 | Saracen et al. |
| 8,295,430 B2 | 10/2012 | Zhu et al. |
| 8,295,435 B2 | 10/2012 | Wang et al. |
| 8,295,906 B2 | 10/2012 | Saunders et al. |
| 8,303,505 B2 | 11/2012 | Webler et al. |
| 8,311,185 B2 | 11/2012 | Seppi et al. |
| 8,331,532 B2 | 12/2012 | Nord et al. |
| 8,457,372 B2 | 6/2013 | Fu et al. |
| 8,461,538 B2 | 6/2013 | Mazin |
| 8,536,547 B2 | 9/2013 | Maurer, Jr. et al. |
| 8,559,596 B2 | 10/2013 | Thomson et al. |
| 8,571,639 B2 | 10/2013 | Mostafavi |
| 8,588,367 B2 | 11/2013 | Busch et al. |
| 8,594,769 B2 | 11/2013 | Mostafavi |
| 8,606,349 B2 | 12/2013 | Rousso et al. |
| 8,641,592 B2 | 2/2014 | Yu |
| 8,745,789 B2 | 6/2014 | Saracen et al. |
| 8,748,825 B2 | 6/2014 | Mazin |
| 8,767,917 B2 | 7/2014 | Ruchala et al. |
| 8,788,020 B2 | 7/2014 | Mostafavi et al. |
| 8,824,630 B2 | 9/2014 | Maurer, Jr. et al. |
| 8,831,706 B2 | 9/2014 | Fu et al. |
| 8,861,672 B2 | 10/2014 | Maltz et al. |
| 8,874,187 B2 | 10/2014 | Thomson et al. |
| 8,917,813 B2 | 12/2014 | Maurer, Jr. |
| 9,155,909 B2 | 10/2015 | Ishikawa |
| 9,205,281 B2 | 12/2015 | Mazin |
| 9,232,928 B2 | 1/2016 | Mostafavi |
| 9,248,312 B2 | 2/2016 | Li et al. |
| 9,283,403 B2 | 3/2016 | Mazin et al. |
| 9,446,264 B2 | 9/2016 | Sawkey et al. |
| 9,616,251 B2 | 4/2017 | Filiberti et al. |
| 9,623,262 B2 | 4/2017 | Vaziri et al. |
| 9,649,509 B2 | 5/2017 | Mazin et al. |
| 9,694,208 B2 | 7/2017 | Mazin et al. |
| 9,731,148 B2 | 8/2017 | Olivera et al. |
| 9,764,161 B2 | 9/2017 | Mazin et al. |
| 9,820,700 B2 | 11/2017 | Mazin |
| 9,849,308 B2 | 12/2017 | Berlinger et al. |
| 9,990,711 B2 | 6/2018 | Lugosi et al. |
| 10,065,049 B2 | 9/2018 | Lugosi et al. |
| 10,143,857 B2 | 12/2018 | Mazin et al. |
| 10,159,852 B2 | 12/2018 | Mazin et al. |
| 10,279,196 B2 | 5/2019 | West et al. |
| 10,327,716 B2 | 6/2019 | Mazin |
| 10,449,389 B2 | 10/2019 | Ollila et al. |
| 10,617,890 B2 | 4/2020 | Mazin et al. |
| 10,646,188 B2 | 5/2020 | Mostafavi et al. |
| 10,688,320 B2 | 6/2020 | Voronenko et al. |
| 10,695,583 B2 | 6/2020 | Mazin et al. |
| 10,695,586 B2 | 6/2020 | Harper et al. |
| 10,702,715 B2 | 7/2020 | Pearce et al. |
| 10,737,118 B2 | 8/2020 | Mostafavi |
| 10,745,253 B2 | 8/2020 | Saracen et al. |
| 10,799,716 B2 | 10/2020 | Morgas et al. |
| 10,806,368 B2 | 10/2020 | Hebert |
| 10,835,761 B2 | 11/2020 | Beriault et al. |
| 10,918,885 B2 | 2/2021 | Haas et al. |
| 10,959,686 B2 | 3/2021 | Mazin |
| 11,033,757 B2 | 6/2021 | Voronenko et al. |
| 11,083,913 B2 | 8/2021 | Lachaine et al. |
| 11,141,607 B2 | 10/2021 | Mazin et al. |
| 11,154,269 B2 | 10/2021 | Shea et al. |
| 11,173,324 B2 | 11/2021 | Paysan et al. |
| 11,278,737 B2 | 3/2022 | Peltola et al. |
| 11,291,858 B2 | 4/2022 | MacDonald et al. |
| 11,309,072 B2 | 4/2022 | Carmi |
| 11,358,008 B2 | 6/2022 | Voronenko et al. |
| 11,369,805 B2 | 6/2022 | Maltz |
| 11,369,806 B2 | 6/2022 | Laurence, Jr. et al. |
| 11,406,846 B2 | 8/2022 | Voronenko et al. |
| 11,478,662 B2 | 10/2022 | Sayeh et al. |
| 11,504,548 B2 | 11/2022 | Fong de los Santos et al. |
| 11,504,550 B2 | 11/2022 | Maolinbay |
| 11,520,415 B2 | 12/2022 | Douglas et al. |
| 11,596,807 B2 | 3/2023 | Maurer et al. |
| 11,617,903 B2 | 4/2023 | Lamb et al. |
| 11,627,920 B2 | 4/2023 | Mazin |
| 11,633,626 B2 | 4/2023 | Voronenko et al. |
| 11,642,027 B2 | 5/2023 | Otto |
| 11,684,801 B2 | 6/2023 | Schadewaldt et al. |
| 11,896,848 B2 | 2/2024 | Janardhanan et al. |
| 12,115,386 B2 | 10/2024 | Voronenko et al. |
| 2002/0051513 A1 | 5/2002 | Pugachev et al. |
| 2002/0163994 A1 | 11/2002 | Jones |
| 2002/0191734 A1 | 12/2002 | Kojima et al. |
| 2003/0036700 A1 | 2/2003 | Weinberg |
| 2003/0058984 A1 | 3/2003 | Susami et al. |
| 2003/0128801 A1 | 7/2003 | Eisenberg et al. |
| 2003/0219098 A1 | 11/2003 | McNutt et al. |

(56) References Cited

U.S. PATENT DOCUMENTS

| | | |
|---|---|---|
| 2003/0235531 A1 | 12/2003 | Adair |
| 2004/0024300 A1 | 2/2004 | Graf |
| 2004/0030246 A1 | 2/2004 | Townsend et al. |
| 2004/0037390 A1 | 2/2004 | Mihara et al. |
| 2004/0057557 A1 | 3/2004 | Nafstadius |
| 2004/0116804 A1 | 6/2004 | Mostafavi |
| 2004/0162457 A1 | 8/2004 | Maggiore et al. |
| 2004/0218719 A1 | 11/2004 | Brown et al. |
| 2005/0201509 A1 | 9/2005 | Mostafavi et al. |
| 2005/0201510 A1 | 9/2005 | Mostafavi |
| 2005/0207531 A1 | 9/2005 | Dempsey et al. |
| 2005/0213705 A1 | 9/2005 | Hoffman |
| 2005/0228255 A1 | 10/2005 | Saracen et al. |
| 2005/0234327 A1 | 10/2005 | Saracen et al. |
| 2006/0002511 A1 | 1/2006 | Miller et al. |
| 2006/0072699 A1 | 4/2006 | Mackie et al. |
| 2006/0113482 A1 | 6/2006 | Pelizzari et al. |
| 2006/0159220 A1 | 7/2006 | Heuscher |
| 2006/0182326 A1 | 8/2006 | Schildkraut et al. |
| 2006/0193435 A1 | 8/2006 | Hara et al. |
| 2006/0237652 A1 | 10/2006 | Kimchy et al. |
| 2007/0003010 A1 | 1/2007 | Guertin et al. |
| 2007/0003123 A1 | 1/2007 | Fu et al. |
| 2007/0014391 A1 | 1/2007 | Mostafavi et al. |
| 2007/0025496 A1 | 2/2007 | Brown et al. |
| 2007/0025513 A1 | 2/2007 | Ghelmansarai |
| 2007/0025524 A1 | 2/2007 | Yue |
| 2007/0053491 A1 | 3/2007 | Schildkraut et al. |
| 2007/0085012 A1 | 4/2007 | Thompson |
| 2007/0133749 A1 | 6/2007 | Mazin et al. |
| 2007/0153969 A1 | 7/2007 | Maschke |
| 2007/0165779 A1 | 7/2007 | Chen et al. |
| 2007/0167801 A1 | 7/2007 | Webler et al. |
| 2007/0237290 A1 | 10/2007 | Mostafavi |
| 2007/0265230 A1 | 11/2007 | Rousso et al. |
| 2007/0265528 A1 | 11/2007 | Xu et al. |
| 2008/0002811 A1 | 1/2008 | Allison |
| 2008/0031404 A1 | 2/2008 | Khamene et al. |
| 2008/0071131 A1 | 3/2008 | Rietzel |
| 2008/0095416 A1 | 4/2008 | Jeung et al. |
| 2008/0128631 A1 | 6/2008 | Suhami |
| 2008/0156993 A1 | 7/2008 | Weinberg et al. |
| 2008/0177179 A1 | 7/2008 | Stubbs et al. |
| 2008/0205588 A1 | 8/2008 | Kim |
| 2008/0230705 A1 | 9/2008 | Rousso et al. |
| 2008/0273659 A1 | 11/2008 | Guertin et al. |
| 2009/0003655 A1 | 1/2009 | Wollenweber |
| 2009/0052623 A1 | 2/2009 | Tome et al. |
| 2009/0088622 A1 | 4/2009 | Mostafavi |
| 2009/0116616 A1 | 5/2009 | Lu et al. |
| 2009/0169082 A1 | 7/2009 | Mizuta et al. |
| 2009/0252291 A1* | 10/2009 | Lu .................. A61N 5/1049 378/65 |
| 2009/0256078 A1 | 10/2009 | Mazin |
| 2009/0309046 A1 | 12/2009 | Balakin |
| 2010/0040197 A1 | 2/2010 | Maniawski et al. |
| 2010/0049030 A1 | 2/2010 | Saunders et al. |
| 2010/0054411 A1 | 3/2010 | Nord et al. |
| 2010/0067660 A1 | 3/2010 | Maurer, Jr. et al. |
| 2010/0074400 A1 | 3/2010 | Sendai |
| 2010/0074408 A1 | 3/2010 | Bert et al. |
| 2010/0074498 A1 | 3/2010 | Breeding et al. |
| 2010/0150309 A1 | 6/2010 | Nord et al. |
| 2010/0166274 A1 | 7/2010 | Busch et al. |
| 2010/0176309 A1 | 7/2010 | Mackie et al. |
| 2010/0198063 A1 | 8/2010 | Huber et al. |
| 2010/0237259 A1 | 9/2010 | Wang |
| 2010/0258138 A1 | 10/2010 | Sorensen et al. |
| 2010/0266099 A1 | 10/2010 | Busch et al. |
| 2011/0006212 A1 | 1/2011 | Shchory et al. |
| 2011/0044429 A1 | 2/2011 | Takahashi et al. |
| 2011/0073763 A1 | 3/2011 | Subbarao |
| 2011/0215248 A1 | 9/2011 | Lewellen et al. |
| 2011/0297833 A1 | 12/2011 | Takayama |
| 2011/0309252 A1 | 12/2011 | Moriyasu et al. |
| 2011/0313232 A1 | 12/2011 | Balakin |
| 2012/0004518 A1 | 1/2012 | D'Souza et al. |
| 2012/0053961 A1 | 3/2012 | Wang et al. |
| 2012/0161014 A1 | 6/2012 | Yamaya et al. |
| 2012/0174317 A1 | 7/2012 | Saracen et al. |
| 2012/0189102 A1 | 7/2012 | Maurer, Jr. et al. |
| 2012/0320055 A1 | 12/2012 | Pekar et al. |
| 2013/0018232 A1 | 1/2013 | D'Souza et al. |
| 2013/0025055 A1 | 1/2013 | Saracen et al. |
| 2013/0060134 A1 | 3/2013 | Eshima et al. |
| 2013/0188856 A1 | 7/2013 | Adler, Jr. et al. |
| 2013/0279658 A1 | 10/2013 | Mazin |
| 2014/0126700 A1 | 5/2014 | Gertner et al. |
| 2014/0163368 A1 | 6/2014 | Rousso et al. |
| 2014/0193336 A1 | 7/2014 | Rousso et al. |
| 2014/0217294 A1 | 8/2014 | Rothfuss et al. |
| 2014/0257096 A1 | 9/2014 | Prevrhal et al. |
| 2014/0371581 A1 | 12/2014 | Mostafavi et al. |
| 2015/0043709 A1 | 2/2015 | Shapiro et al. |
| 2015/0055849 A1 | 2/2015 | Galavis et al. |
| 2015/0087960 A1 | 3/2015 | Treffert |
| 2015/0355347 A1 | 12/2015 | Pratx |
| 2015/0360056 A1 | 12/2015 | Xing et al. |
| 2016/0023019 A1 | 1/2016 | Filiberti et al. |
| 2016/0038767 A1 | 2/2016 | Wiersma et al. |
| 2016/0296766 A1 | 10/2016 | El Fakhri et al. |
| 2016/0361566 A1 | 12/2016 | Larkin et al. |
| 2017/0007447 A1 | 1/2017 | Goldshleger et al. |
| 2017/0023494 A1 | 1/2017 | Yu et al. |
| 2017/0087385 A1 | 3/2017 | Miettinen et al. |
| 2017/0209715 A1 | 7/2017 | Ruebel et al. |
| 2018/0154179 A1 | 6/2018 | Ollila et al. |
| 2018/0345042 A1 | 12/2018 | Voronenko et al. |
| 2018/0369611 A1 | 12/2018 | Owens et al. |
| 2019/0001152 A1 | 1/2019 | O'Connor et al. |
| 2019/0054315 A1 | 2/2019 | Isola et al. |
| 2019/0054320 A1 | 2/2019 | Owens et al. |
| 2019/0070436 A1 | 3/2019 | Willcut et al. |
| 2019/0130569 A1 | 5/2019 | Liu et al. |
| 2019/0217123 A1 | 7/2019 | West et al. |
| 2019/0279094 A1 | 9/2019 | Baughman et al. |
| 2019/0357859 A1 | 11/2019 | Mazin |
| 2019/0381338 A1 | 12/2019 | Voronenko et al. |
| 2020/0206536 A1 | 7/2020 | Wang et al. |
| 2021/0196212 A1 | 7/2021 | Mazin |
| 2021/0236854 A1 | 8/2021 | Voronenko et al. |
| 2021/0327560 A1 | 10/2021 | Carmi |
| 2021/0339047 A1 | 11/2021 | Janardhanan et al. |
| 2022/0096867 A1 | 3/2022 | Mazin et al. |
| 2022/0126117 A1 | 4/2022 | Voronenko et al. |
| 2022/0218204 A1 | 7/2022 | Adler, Jr. et al. |
| 2022/0395707 A1 | 12/2022 | Laurence, Jr. et al. |
| 2023/0067048 A1 | 3/2023 | Voronenko et al. |
| 2023/0285777 A1 | 9/2023 | Bassalow et al. |
| 2024/0104767 A1 | 3/2024 | Voronenko et al. |
| 2024/0316363 A1 | 9/2024 | Voronenko et al. |

FOREIGN PATENT DOCUMENTS

| | | |
|---|---|---|
| CN | 1824342 A | 8/2006 |
| CN | 1960780 A | 5/2007 |
| CN | 101013095 A | 8/2007 |
| CN | 101305297 A | 11/2008 |
| CN | 101970043 A | 2/2011 |
| CN | 103180014 A | 6/2013 |
| CN | 104284697 A | 1/2015 |
| CN | 105658279 A | 6/2016 |
| CN | 106563211 A | 4/2017 |
| CN | 107072595 A | 8/2017 |
| CN | 107072628 A | 8/2017 |
| DE | 10 2008 053321 A1 | 5/2010 |
| JP | 09-33658 A | 2/1997 |
| JP | 09-189769 A2 | 7/1997 |
| JP | H-11-290466 A | 10/1999 |
| JP | 2000-105279 A | 4/2000 |
| JP | 2001-340474 A | 12/2001 |
| JP | 2003-534823 A | 11/2003 |
| JP | 2004-073404 A | 3/2004 |
| JP | 2004-513735 A | 5/2004 |

(56) References Cited

FOREIGN PATENT DOCUMENTS

| | | |
|---|---|---|
| JP | 2005-261941 A | 9/2005 |
| JP | 2006-145281 A | 6/2006 |
| JP | 2007-502166 A | 2/2007 |
| JP | 2007-507246 A | 3/2007 |
| JP | 2009-005440 A | 1/2009 |
| JP | 2009-544101 A | 12/2009 |
| JP | 2010-517655 A | 5/2010 |
| JP | 2011-514213 A | 5/2011 |
| JP | 2012-506734 A | 3/2012 |
| JP | 6210972 B2 | 10/2017 |
| JP | 2017-199876 A | 11/2017 |
| JP | 6571816 B2 | 9/2019 |
| JP | 6796886 B2 | 12/2020 |
| JP | 7274773 B2 | 5/2023 |
| WO | WO-2005/110495 A1 | 11/2005 |
| WO | WO-2006/051531 | 5/2006 |
| WO | WO-2006/086765 | 8/2006 |
| WO | WO-2007/120674 | 10/2007 |
| WO | WO-2008/024463 | 2/2008 |
| WO | WO-2008/127368 | 10/2008 |
| WO | WO-2009/111580 | 9/2009 |
| WO | WO-2010/015358 A1 | 2/2010 |
| WO | WO-2010/018477 | 2/2010 |
| WO | WO-2010/110255 A1 | 9/2010 |
| WO | WO-2016/023786 A1 | 2/2016 |
| WO | WO-2016/064750 A1 | 4/2016 |
| WO | WO-2018/024487 A1 | 2/2018 |
| WO | WO-2018/183748 A1 | 10/2018 |
| WO | WO-2020/144134 A1 | 7/2020 |
| WO | WO-2021/011207 A1 | 1/2021 |
| WO | WO-2022/031750 A1 | 2/2022 |
| WO | WO-2022/098794 A1 | 5/2022 |
| WO | WO-2022/182681 | 9/2022 |
| WO | WO-2023/070088 A1 | 4/2023 |
| WO | WO-2024/107734 A1 | 5/2024 |
| WO | WO-2024/206384 A1 | 10/2024 |

OTHER PUBLICATIONS

Black, Q.C. et al. (2004). "Defining a Radiotherapy Target with positron emission tomography," Int. J. Radiation Oncology Biol. Phys. 60:1272-1282.
Bush, S. (Sep. 2020). "Add noise for clearer signals," located at https://www.electronicsweekly.com/news/research-news/add-noise-clearer-signals-2020-09/, 4 total pages.
Corrected Notice of Allowability mailed on Feb. 3, 2021, for U.S. Appl. No. 16/425,416, filed May 29, 2019, 2 pages.
Corrected Notice of Allowability mailed on Mar. 13, 2023, for U.S. Appl. No. 17/235,812, filed Apr. 20, 2021, 4 pages.
Corrected Notice of Allowability mailed on Mar. 16, 2023, for U.S. Appl. No. 17/203,532, filed Mar. 16, 2021, 2 pages.
Erdi, Y.E. (2007). "The use of PET for radiotherapy," *Curr. Medical Imaging Reviews* 3(1):3-16.
Extended European Search Report mailed on Mar. 31, 2017, for European Application No. 09 719 473.2, filed on Mar. 9, 2009, 8 pages.
Extended European Search Report mailed on Oct. 7, 2015, for European Application No. 12 763 280.0, filed on Mar. 30, 2012, 11 pages.
Extended European Search Report mailed on Nov. 21, 2018, for European Application No. 18 168 947.2, filed on Mar. 30, 2012, 8 pages.
Extended European Search Report mailed on Oct. 30, 2020, for EP Application No. 20 179 036.7, filed on Mar. 9, 2009, 12 pages.
Extended European Search Report mailed on Feb. 3, 2021, for EP Application No. 18 810 297.4, filed on May 30, 2018, 4 pages.
Final Office Action mailed on Aug. 15, 2012, for U.S. Appl. No. 13/209,275, filed on Aug. 12, 2011, 8 pages.
Final Office Action mailed on Aug. 2, 2018, for U.S. Appl. No. 15/684,710, filed Aug. 23, 2017, 8 pages.

Internal Atomic Energy Agency (Oct. 2008). "The Role of PET/CT in Radiation Treatment Planning for Cancer Patient Treatment," located at https://www-pub.iaea.org/MTCD/Publications/PDF/te_1603_web.pdf, 40 total pages.
International Search Report mailed on May 4, 2009, for PCT Application No. PCT/US2009/01500, filed on Mar. 9, 2009, 3 pages.
International Search Report mailed on Jul. 20, 2012, for PCT Patent Application No. PCT/US2012/31704, filed on Mar. 30, 2012, 2 pages.
International Search Report mailed on Jan. 17, 2018, for PCT Application No. PCT/US2017/061728, filed on Nov. 15, 2017, 2 pages.
International Search Report mailed on Oct. 3, 2018, for PCT Application No. PCT/US2018/035188, filed on May 30, 2018, 4 pages.
International Search Report mailed on Apr. 23, 2020, for PCT Application No. PCT/US2020/013927, filed on Jan. 16, 2020, 3 pages.
International Search Report mailed on Dec. 1, 2020, for PCT Application No. PCT/US2020/040774, filed on Jul. 2, 2020, 4 pages.
International Search Report mailed on Mar. 10, 2022, for PCT Application No. PCT/US2021/057948, filed on Nov. 3, 2021, 4 pages.
International Search Report mailed on Dec. 16, 2021, for PCT Application No. PCT/US2021/044405, filed on Aug. 3, 2021, 4 pages.
International Search Report mailed on Aug. 24, 2022, for PCT Application No. PCT/US2022/017375, filed on Feb. 22, 2022, 7 pages.
Non-Final Office Action mailed on Feb. 24, 2017, for U.S. Appl. No. 15/069,390, filed Mar. 14, 2016, 6 pages.
Non-Final Office Action mailed on Feb. 21, 2018, for U.S. Appl. No. 15/684,710, filed Aug. 23, 2017, 10 pages.
Non-Final Office Action mailed on Mar. 27, 2018, for U.S. Appl. No. 15/684,693, filed Aug. 23, 2017, 7 pages.
Non-Final Office Action mailed on Aug. 30, 2019, for U.S. Appl. No. 16/193,725, filed Nov. 16, 2018, 5 pages.
Non-Final Office Action mailed on Sep. 19, 2019, for U.S. Appl. No. 16/217,417, filed Dec. 12, 2018, 7 pages.
Non-Final Office Action mailed on Dec. 6, 2019, for U.S. Appl. No. 15/993,325, filed May 30, 2018, 8 pages.
Non-Final Office Action mailed on Oct. 29, 2020, for U.S. Appl. No. 16/834,956, filed Mar. 30, 2020, 7 pages.
Non-Final Office Action mailed on Dec. 22, 2020, for U.S. Appl. No. 16/554,258, filed Aug. 28, 2019, 11 pages.
Non-Final Office Action mailed on Dec. 21, 2021, for U.S. Appl. No. 16/412,780, filed May 15, 2019, 15 pages.
Non-Final Office Action mailed on Jul. 5, 2022, for U.S. Appl. No. 17/203,532, filed Mar. 16, 2021, 13 pages.
Non-Final Office Action mailed on Aug. 30, 2022, for U.S. Appl. No. 17/235,812, filed Apr. 20, 2021, 8 pages.
Non-Final Office Action mailed on Jan. 27, 2023, for U.S. Appl. No. 17/485,059, filed Sep. 24, 2021, 11 pages.
Notice of Allowance mailed on Jul. 25, 2011, for U.S. Appl. No. 12/367,679, filed Feb. 9, 2009, 7 pages.
Notice of Allowance mailed on Apr. 9, 2014, for U.S. Appl. No. 13/895,255, filed May 15, 2013, 7 pages.
Notice of Allowance mailed on Oct. 27, 2015, for U.S. Appl. No. 14/278,973, filed May 15, 2014, 8 pages.
Notice of Allowance mailed on Mar. 27, 2013, for U.S. Appl. No. 13/209,275, filed Aug. 12, 2011, 9 pages.
Notice of Allowance mailed on Oct. 5, 2017, for U.S. Appl. No. 14/951,194, filed Nov. 24, 2015, 11 pages.
Notice of Allowance mailed on May 18, 2017, for U.S. Appl. No. 15/069,390, filed Mar. 14, 2016, 5 pages.
Notice of Allowance mailed on Jul. 19, 2017, for U.S. Appl. No. 15/499,671, filed Apr. 27, 2017, 8 pages.
Notice of Allowance mailed on Oct. 3, 2018, for U.S. Appl. No. 15/684,693, filed Aug. 23, 2017, 5 pages.
Notice of Allowance mailed on Oct. 25, 2018, for U.S. Appl. No. 15/684,710, filed Aug. 23, 2017, 7 pages.

(56) References Cited

OTHER PUBLICATIONS

Notice of Allowance mailed on Apr. 4, 2019, for U.S. Appl. No. 15/807,383, filed Nov. 8, 2017, 11 pages.
Notice of Allowance mailed on Jan. 21, 2020, for U.S. Appl. No. 16/193,725, filed Nov. 16, 2018, 7 pages.
Notice of Allowance mailed on Mar. 13, 2020, for U.S. Appl. No. 16/217,417, filed Dec. 12, 2018, 6 pages.
Notice of Allowance mailed on Apr. 20, 2020, for U.S. Appl. No. 15/993,325, filed May 30, 2018, 7 pages.
Notice of Allowance mailed on Jan. 12, 2021, for U.S. Appl. No. 16/425,416, filed May 29, 2019, 13 pages.
Notice of Allowance mailed on Jun. 21, 2021, for U.S. Appl. No. 16/834,956, filed Mar. 30, 2020, 7 pages.
Notice of Allowance mailed on Jun. 8, 2022, for U.S. Appl. No. 16/412,780, filed May 15, 2019, 8 pages.
Notice of Allowance mailed on Dec. 15, 2022, for U.S. Appl. No. 17/203,532, filed Mar. 16, 2021, 8 pages.
Notice of Allowance mailed on Feb. 1, 2023, for U.S. Appl. No. 17/235,812, filed Apr. 20, 2021, 7 pages.
Persson, G.F. et al. (Sep. 2013). "Stability of percutaneously implanted markers for lung stereotactic radiotherapy," J. Appl. Clin. Med. Phys. 14:187-195.
Shirvani, S.M. et al. (Jan. 2021). "Biology-guided radiotherapy: redefining the role of radiotherapy in metastatic cancer," Br. J. Radiol. 94:20200873, 10 total pages.
Wang, D. et al. (2006). "Initial experience of FDG-PET/CT guided IMRT of head-and-neck carcinoma," Int. J. Radiation Oncology Biol. Phys. 65:143-151.
Written Opinion of the International Searching Authority mailed on May 4, 2009, for PCT Application No. PCT/US2009/01500, filed on Mar. 9, 2009, 5 pages.
Written Opinion mailed on Jul. 20, 2012, for PCT Patent Application No. PCT/US2012/31704, filed on Mar. 30, 2012, 10 pages.
Written Opinion of the International Searching Authority mailed on Jan. 17, 2018, for PCT Application No. PCT/US2017/061728, filed on Nov. 15, 2017, 7 pages.
Written Opinion of the International Searching Authority mailed on Oct. 3, 2018, for PCT Application No. PCT/US2018/035188, filed on May 30, 2018, 28 pages.
Written Opinion of the International Searching Authority mailed on Apr. 23, 2020, for PCT Application No. PCT/US2020/013927, filed on Jan. 16, 2020, 4 pages.
Written Opinion of the International Searching Authority mailed on Dec. 1, 2020, for PCT Application No. PCT/US2020/040774, filed on Jul. 2, 2020, 8 pages.
Written Opinion of the International Searching Authority mailed on Mar. 10, 2022, for PCT Application No. PCT/US2021/057948, filed on Nov. 7, 2021, 7 pages.
Written Opinion of the International Searching Authority mailed on Dec. 16, 2021, for PCT Application No. PCT/US2021/044405, filed on Aug. 3, 2021, 5 pages.
Written Opinion of the International Searching Authority mailed on Aug. 24, 2022, for PCT Application No. PCT/US2022/017375, filed on Feb. 22, 2022, 11 pages.
Chetty, I.J. et al. (Apr. 2004). "Accounting for center-of-mass target motion using convolution methods in Monte Carlo-based dose calculations of the lung," Med. Phys. 31(4): 925-932.
Extended European Search Report mailed on Jun. 23, 2023, for EP Application No. 20 840 804.7, filed on Jul. 2, 2020, 7 pages.
Extended European Search Report mailed on Jan. 24, 2024, for EP Application No. 23 160 060.2, filed on Mar. 9, 2009, 12 pages.
Extended European Search Report mailed on Jul. 29, 2024, for EP Application No. 21 853 184.6, filed on Aug. 3, 2021, 5 pages.
Final Office Action mailed on Aug. 21, 2023, for U.S. Appl. No. 17/485,059, filed Sep. 24, 2021, 10 pages.
Final Office Action mailed on Jul. 1, 2024, for U.S. Appl. No. 17/485,059, filed Sep. 24, 2021, 10 pages.
Gregoire, V et al. (2007). "PET-based treatment planning in radiotherapy: a new standard?" J. Nucl. Med. 48(Suppl 1): 68S-77S.
International Search Report mailed on Apr. 5, 2023, for PCT Application No. PCT/US2022/078511, filed on Oct. 21, 2022, 6 pages.
International Search Report mailed on Apr. 26, 2024, for PCT Application No. PCT/US2023/079652, filed on Nov. 14, 2023, 7 pages.
International Search Report mailed on Jul. 18, 2024, for PCT Application No. PCT/US2024/021603, filed on Mar. 27, 2024, 4 pages.
Non-Final Office Action mailed on Dec. 13, 2023, for U.S. Appl. No. 17/485,059, filed Sep. 24, 2021, 10 pages.
Non-Final Office Action mailed on Jan. 16, 2024, for U.S. Appl. No. 18/178,431, filed Mar. 3, 2023, 16 pages.
Non-Final Office Action mailed on Sep. 23, 2024, for U.S. Appl. No. 17/855,691, filed Jun. 30, 2022, 15 pages.
Notice of Allowance mailed on Dec. 13, 2023, for U.S. Appl. No. 17/375,586, filed Jul. 14, 2021, 12 pages.
Notice of Allowance mailed on Aug. 13, 2024, for U.S. Appl. No. 18/178,431, filed Mar. 3, 2023, 9 pages.
Notice of Allowance mailed on May 9, 2024, for U.S. Appl. No. 17/571,273, filed Jan. 7, 2022, 15 pages.
Shalchian, B et al. (2009). "Assessment of the Wavelet Transform in Reduction of Noise from Simulated PET Images," Journal of Nuclear Medicine Technology 37:223-228.
Staff, N.R.C. (1996). "Mathematics and Physics of Emerging Biomedical imaging," National Academies Press, Washington, D.C., 261 pages.
Supplemental Notice of Allowability mailed on Aug. 8, 2024, for U.S. Appl. No. 17/571,273, filed Jan. 7, 2022, 2 pages.
Written Opinion of the International Searching Authority mailed on Apr. 5, 2023, for PCT Application No. PCT/US2022/078511, filed on Oct. 21, 2022, 6 pages.
Written Opinion of the International Searching Authority mailed on Apr. 26, 2024, for PCT Application No. PCT/US2023/079652, filed on Nov. 14, 2023, 9 pages.
Written Opinion of the International Searching Authority mailed on Jul. 18, 2024, for PCT Application No. PCT/US2024/021603, filed on Mar. 27, 2024, 6 pages.

* cited by examiner

Tumor POV space

Static space (patient POV)

Tumor POV space

Static space (patient POV)

MULTI-SENSOR GUIDED RADIATION THERAPY

CROSS-REFERENCE TO RELATED APPLICATIONS

This application is a bypass continuation of PCT Patent Application No. PCT/US2021/044405, filed Aug. 3, 2021, entitled "MULTI-SENSOR GUIDED RADIATION THERAPY," which is hereby incorporated herein by reference in its entirety, and which claims priority to U.S. Provisional Patent Application No. 63/062,792 filed Aug. 7, 2020, the disclosure of which is hereby incorporated by reference in its entirety.

BACKGROUND

Radiation therapy is a non-invasive procedure that involves applying high levels of radiation to a tumor or lesion. Such high levels of radiation may slow or otherwise halt the growth of cancer cells. Some radiation therapy systems have a therapeutic radiation source that is movable around a patient so that radiation is directed to the tumor from various positions and/or angles around the patient. The patient is usually positioned on a platform that may or may not be moved in concert with the therapeutic radiation source to irradiate the tumor.

It can be challenging to apply high levels of radiation to a tumor while limiting radiation exposure to surrounding healthy tissue. This difficulty is further exacerbated by the fact that radiation is invisible, and the tumor is usually located within the patient. Although a treatment plan is generated based on planning images of the patient and the tumor, a treatment session usually occurs days or weeks later, in which time, the location of the tumor within the patient may have changed. Some radiation therapy systems have an imaging system that can be used to acquire images of the patient and/or the tumor so that their locations can be determined at the start of a treatment session. Information about the location of the patient, the tumor, and other patient structures may be compared with their location in the planning images. If there are any discrepancies, the patient is moved (e.g., by moving the platform and/or adjusting the patient's posture and/or position on the platform) so that the patient (and/or tumor) location matches the location in the planning images. This helps ensure that the therapeutic radiation source irradiates the tumor in accordance with the treatment plan.

However, the patient may move during a treatment session and such movement can cause the tumor to move and change its location from its original location at the start of the treatment session. In some cases, the motion may be due to unavoidable physiological processes, such as breathing, digestion, and the like, and/or unexpected patient motions (e.g., the patient shifts position due to discomfort, coughing). An image acquired at the beginning of a treatment session is unable to capture changes in tumor location after the treatment session has started (i.e., when the therapeutic radiation source begins emitting radiation to the tumor). Some radiotherapy treatment planning methods may account for tumor motion due to predictable, periodic physiological motion (such as breathing) by defining a motion envelope of the tumor based on the planning images. This results in a treatment plan that delivers a high level of radiation to the region encompassed by the motion envelope, ensuring that a sufficiently ablative level of radiation is delivered to the tumor. However, this method may also result in the irradiation of healthy tissue that happens to be located within the motion envelope.

Accordingly, improved methods of radiotherapy treatment planning and delivery are desirable to deliver tumoricidal levels of radiation to patient target regions while limiting the radiation exposure of healthy tissue are desired.

SUMMARY

Disclosed herein are methods for radiotherapy treatment planning and delivery that use sensor data from one or more target region sensors. In some variations, the one or more target region sensors may be one or more patient sensors. Radiotherapy treatment planning methods may comprise generating a sensor characterization image based on a sensor characterization probability density function (PDF) of a target sensor and calculating a set of firing filters that may be applied to sensor data acquired during a radiation delivery session (e.g., a non-therapeutic quality assurance or QA session, or alternatively a treatment session). A sensor characterization PDF of a target sensor may represent the noise characteristics and/or variabilities and/or error profile of the target sensor. The firing filters may be shift-invariant. Target sensors may comprise one or more position sensors, image sensors, and the like. The radiotherapy delivery methods described herein may comprise acquiring one or more sensor data readings from the target sensor, calculating a radiation fluence map for delivery by convolving an image generated from the sensor data reading(s) with a treatment plan firing filter, and delivering radiation according to the calculated radiation fluence map. Image and/or position sensor data may be acquired frequently during a radiation delivery session (e.g., a non-therapeutic QA session in the absence of a patient, or alternatively a treatment session in the presence of a patient), and may, for example, be acquired within seconds or milliseconds before a radiation beam is emitted toward the target region. In some variations, the target region may be a patient target region to which therapeutic radiation is delivered during a treatment session. Frequent acquisition of image and/or position sensor data may be used by the radiation therapy system to adjust the radiation fluence map in real-time to account for patient and/or tumor motion to help guide radiation delivery to the actual location of the tumor.

In some variations, radiotherapy treatment planning may use sensor data from multiple target region sensors to calculate multiple sets of corresponding firing filters. For example, a radiotherapy treatment planning method may comprise generating a first sensor characterization image based on a first sensor characterization probability density function (PDF) of a first target sensor, generating a second sensor characterization image based on a second sensor characterization PDF of a second target sensor, calculating a first set of firing filters that may be applied to sensor data from the first target sensor acquired during a radiation delivery session (e.g., a QA or treatment session), and calculating a second set of firing filters that may be applied to sensor data from the second target sensor acquired during a radiation delivery session (e.g., a QA or treatment session). The first target sensor and the second target sensor may be the same sensor type and/or may be different sensor types. During a radiation delivery session, sensor data may be acquired from both the first target sensor and the second target sensor and used to generate sensor data images which are convolved with their respective firing filters and combined to generate a radiation fluence map for delivery. In some variations, a radiotherapy delivery method may comprise acquiring a first sensor data reading from the first target sensor, acquiring a second sensor data reading from the second target sensor, calculating a radiation fluence map for delivery by summing the convolution of a first image generated from the first sensor data reading with the first firing filter and the convolution of a second image generated from the second sensor data reading with the second firing filter, and delivering radiation according to the calculated radiation fluence map. Calculating the radiation fluence for delivery using real-time acquired data from two or more target sensors may help provide an accurate indication of the location of the target region(s), and/or help facilitate precise delivery of therapeutic radiation to the target region(s).

Also disclosed herein are methods for radiotherapy treatment planning that use patient imaging data and position data to calculate firing filters that may be applied to an image acquired during a radiation delivery session (e.g., a QA or treatment session) to calculate a radiation fluence map for delivery. In some variations, a radiotherapy treatment planning method may comprise generating a sensor characterization image based on a sensor characterization PDF that comprises a plurality of position values that represent the location of the centroid of the target region over time and calculating firing filters based on the sensor characterization image. The sensor characterization image may comprise one or more motion dwell histograms of the target region. The position values of the centroid may be determined from any appropriate imaging modality, for example, 4-D CT imaging data. A radiotherapy delivery method may comprise acquiring imaging data from an image sensor, generating an image from the acquired imaging data, and calculating a radiation fluence map for delivery by convolving the generated image with a firing filter. The method may then comprise delivering radiation according to the calculated radiation fluence map to the target region. Calculating the firing filters based on a sensor characterization PDF that comprises a plurality of position values that represent the location of the centroid of the target region over time may result in a treatment plan that delivers the prescribed tumoricidal dose to the target region while reducing the irradiation of surrounding healthy tissue.

One variation of a method for radiation delivery comprises acquiring a sensor data reading from a target sensor, generating a sensor image from the sensor data reading, calculating a radiation fluence map for delivery to a target region by convolving the sensor image with a shift-invariant firing filter derived from a sensor characterization probability density function (PDF) of the target sensor, and delivering radiation according to the calculated radiation fluence map to the target region. The sensor characterization PDF may be a sensor error characterization PDF that represents a rate of sensor data errors and/or a rate of sensor data variability. For example, the sensor characterization PDF may comprise one or more of: a 1-D plot of sensor data, a 2-D plot of sensor data, and/or a 3-D plot of sensor data, and a histogram representing sensor data variability. In some variations, the target sensor may be a position sensor. For example, the position sensor may comprise a target region position sensor, and/or the position sensor may comprise an X-ray projector system that is configured to track an implantable fiducial. The sensor image may be a delta function, a gaussian function, and/or a truncated gaussian function that is centered at a location that corresponds to the position sensor data reading. Some methods may comprise attaching an optical fiducial to a patient's skin and tracking the optical fiducial using an optical imaging system.

In some variations, the target sensor may be a null position sensor where the sensor data reading is a constant position value that represents a centroid of the target region, and the sensor characterization PDF of the null position sensor comprises a plurality of position values that represent a location of the centroid of the target region over time. The sensor image may be a delta function, a gaussian function, and/or a truncated gaussian function that is centered at a location that corresponds to the position sensor data reading. The sensor characterization PDF may comprise a motion dwell histogram of the target region. The plurality of position values may be determined, for example, using 4-D CT imaging data.

In some variations, the shift-invariant firing filter may correspond to a firing position of a therapeutic radiation source and calculating the fluence for delivery may comprise calculating a fluence for delivery at the firing position by convolving a projection of the sensor image on the firing position with the shift-invariant firing filter for the firing position. The target sensor may comprise one or more image sensors, the sensor data reading may comprise imaging data, and the sensor characterization PDF of the target sensor may comprise an image generated from the imaging data. The one or more image sensors may comprise an image sensor selected from the group consisting of PET sensors, MRI sensors, and CT sensors.

In some variations, the target sensor may be a first target sensor, the sensor data reading may be a first sensor data reading, the image may be a first sensor data image, the shift-invariant firing filter may be a first shift-invariant firing filter, and the sensor characterization PDF may be a first sensor characterization PDF, and the method may further comprise acquiring a second sensor data reading from a second target sensor, generating a second sensor data image from the second sensor data reading, and where calculating the fluence map for delivery may comprise summing (a) the convolution of the first sensor data image with the first shift-invariant firing filter, and (b) a convolution of the second sensor data image with a second shift-invariant firing filter derived from a second sensor characterization PDF of the second target sensor. The first target sensor data reading may contain a first type of data and the second target sensor data reading may contain a second type of data that is different from the first type of data. The second sensor characterization PDF may be, for example, a sensor error characterization PDF. The second target sensor may be a position sensor. In some variations, the first target sensor data reading may comprise positron annihilation emission path data and the second target sensor data reading may comprise target region location data. The first target sensor data reading may comprise partial imaging data and the second target sensor data reading may comprise target region location data. The first target sensor data reading may comprise at least one of 3-D PET imaging data, 2-D X-ray imaging data, projection imaging data, fluoroscopy imaging data, CT imaging data, and MR imaging data, and the second target sensor data reading may comprise target region location data. In some variations, the shift-invariant firing filter may correspond to a firing position of a therapeutic radiation source and calculating the fluence for delivery may comprise calculating a fluence for delivery at the firing position by projecting the sensor data reading on the firing position, generating a second sensor image of the projected sensor data reading, and convolving the second sensor image with the shift-invariant firing filter for the firing position.

Also described herein are variations of radiotherapy systems. One variation of a radiotherapy system may comprise a patient platform, a therapeutic radiation source movable to one or more firing positions about the patient platform, a target sensor system comprising a target sensor that acquires sensor data, and a controller in communication with the therapeutic radiation source and the target sensor system, where the controller is configured to calculate a radiation fluence map for delivery to a target region by convolving an image generated from sensor data with a shift-invariant firing filter derived from a sensor characterization PDF of the target sensor, and wherein the controller is configured to deliver radiation according to the calculated radiation fluence map. The target sensor may be a first target sensor and the target sensor system may comprise a second target sensor. In some variations, at least one of the first target sensor and the second target sensor may be a position sensor configured to be coupled to a patient disposed on the patient platform. For example, the position sensor may be configured to be coupled to a target region. In some variations, the position sensor may comprise an optical imaging system configured to track an optical fiducial that is attached to a patient's skin, and the target sensor system may further comprise an optical camera configured to detect a position of the optical fiducial. The sensor characterization PDF may be a sensor error characterization PDF that represents a rate of sensor data errors or may represent a rate of sensor data variability. For example, the sensor characterization PDF may comprise one or more of: a 1-D plot of sensor data, a 2-D plot of sensor data, and/or a 3-D plot of sensor data, and a histogram representing sensor data variability. The image generated from the position sensor data may be a delta function, a gaussian function, and/or a truncated gaussian function that is centered at a location that corresponds to the position sensor data. Alternatively, or additionally, the target sensor may comprise one or more image sensors, the sensor data may comprise imaging data, and the sensor characterization PDF of the target sensor may comprise an image. The one or more image sensors may comprise an image sensor selected from the group consisting of PET sensors, MRI sensors, and CT sensors. The controller may be configured to receive a first sensor data reading from the first target sensor and a second sensor data reading from the second target sensor, where the shift-invariant firing filter is a first shift-invariant firing filter for the first target sensor, and the sensor characterization PDF is a first sensor characterization PDF for the first target sensor, and where the controller may be further configured to calculate the fluence map for delivery by summing (a) the convolution of the first sensor data image with the first shift-invariant firing filter, and (b) a convolution of a second image generated from the second sensor data with a second shift-invariant firing filter derived from a second sensor characterization PDF of the second target sensor. The first target sensor may be a first type of sensor and the second target sensor may be a second type of sensor that is different from the first type. The second target sensor may be a position sensor. In some variations, the first target sensor may be a positron annihilation emission path sensor and the second target sensor may be a target region position sensor. Alternatively, or additionally, the first target sensor may be an image sensor and the second target sensor may be a position sensor. The first target sensor may comprise at least one of a 3-D PET sensor, 2-D X-ray sensor, projection image sensor, fluoroscopy image sensor, CT image sensor, and MR sensor, and the second target sensor may comprise a position sensor.

Described herein are methods for treatment planning using target sensor data. A method for sensor-based treatment planning may comprise generating sensor characterization images $N_i$ based on a sensor characterization PDF of a target sensor for each of i firing positions, and calculating shift-invariant firing filters $p_i$ for each of i firing positions based on the sensor characterization images $N_i$ by iterating through values for $p_i$ such that the following conditions are met:

$$D = A \cdot \begin{bmatrix} p_0 * N_0 \\ \vdots \\ p_{i-1} * N_{i-1} \end{bmatrix}$$

where D is a prescribed dose for a target region and A is a known dose calculation matrix for the target region.

The methods for generating treatment plans described herein are carried out in the absence of a patient. These treatment planning methods alone do not include the delivery of therapeutic radiation to a patient.

The target sensor may be a position sensor, the sensor characterization PDF may comprise one or more of: a 1-D plot of position sensor data, a 2-D plot of position sensor data, a 3-D plot of position sensor data, and a histogram representing position sensor data variability, and the sensor characterization images $N_i$ may comprise one or more of: position sensor error data and a position sensor error histogram. The position sensor data may comprise coordinates in space. In some variations, calculating shift-invariant firing filters $p_i$ may further comprise iterating through values for $p_i$ to minimize a cost function C(D,F) derived from clinician-defined constraints and objectives for the prescribed dose D and a radiation fluence map F. In some variations, calculating shift-invariant firing filters $p_i$ may further comprise iterating through values for $p_i$ to minimize a cost function C(D,F) derived from clinician-defined constraints and objectives for the prescribed dose D and a radiation fluence map F.

In some variations, the target sensor may be a null position sensor that has a constant position value that represents a centroid of the target region, and the sensor characterization PDF may comprise a plurality of position values that represent the location of the centroid of the target region over time, and where generating the sensor characterization images $N_i$ may comprise generating motion dwell histograms of the target region. The plurality of position values may be determined using 4-D CT imaging data. In some treatment planning methods, generating the sensor characterization images $N_i$ may comprise generating inverted motion dwell histograms of the target region. In some variations, the target sensor may be an image sensor, the sensor characterization PDF may comprise a plurality of image sensor data and generating the sensor characterization images $N_i$ may comprise combining the plurality of image sensor data. The plurality of image sensor data may comprise at least one of 3-D PET imaging data, 2-D X-ray imaging data, projection imaging data, fluoroscopy imaging data, CT imaging data, and MR imaging data. The target sensor may be a first target sensor, the sensor characterization images $N_i$ may be a first set of sensor characterization images and the shift-invariant firing filters $p_i$ may be a first set of shift-invariant firing filters, and the method further may comprise generating a second set of sensor characterization images $M_i$ based on a sensor characterization PDF of a second target sensor for each of i firing positions, and calculating the first set of shift-invariant firing filters $p_i$ and a second set of shift-invariant firing filters $q_i$ for each of i firing positions based on the first set of sensor characterization images $N_i$ and the second set of sensor characterization images $M_i$ by iterating through values for $p_i$ and $q_i$ such that the following conditions are met:

$$D = A \cdot \begin{bmatrix} p_0 * N_0 + q_0 * M_0 \\ \vdots \\ p_{i-1} * N_{i-1} + q_{i-1} * M_{i-1} \end{bmatrix}.$$

In some variations, calculating shift-invariant firing filters $p_i$ and $q_i$ may further comprise iterating through values for $p_i$ and $q_i$ to minimize a cost function $C(D,F)$ derived from clinician-defined constraints and objectives for the prescribed dose D and a radiation fluence map F. The first target sensor may be a first position sensor and the second target sensor may be a second position sensor. In some variations, each of the sensor characterization PDFs of the first and second position sensors may comprise one or more of: a 1-D plot of position sensor data, a 2-D plot of position sensor data, and/or a 3-D plot of position sensor data, and a histogram representing position sensor data variability, and the sensor characterization images $N_i$ and $M_i$ may comprise motion dwell histograms of the target region. The position sensor data of the first position sensor and the second position sensor may comprise coordinates in space. Alternatively, the first target sensor may be a first image sensor and the second target sensor may be a second image sensor. Each of the sensor characterization PDFs of the first image sensor and the second image sensor may comprise a plurality of image sensor data and generating the sensor characterization images $N_i$ and $M_i$ may comprise combining the plurality of image sensor data from the first image sensor and the second image sensor, respectively. The plurality of image sensor data from the first image sensor and the second image sensor may comprise at least one of 3-D PET imaging data, 2-D X-ray imaging data, projection imaging data, fluoroscopy imaging data, CT imaging data, and MR imaging data.

In some variations, the first target sensor may be a position sensor and the second target sensor may be an image sensor. The sensor characterization PDF of the position sensor may comprise one or more of a 1-D plot of position sensor data, a 2-D plot of position sensor data, and/or a 3-D plot of position sensor data, and a histogram representing position sensor data variability, and the sensor characterization PDF of the image sensor may comprise a plurality of image sensor data. For example, the sensor characterization images $N_i$ may be motion dwell histograms of the target region, and the sensor characterization images $M_i$ may be a combination of the plurality of image sensor data. The position sensor data may comprise coordinates in space and the plurality of image sensor data may comprise at least one of 3-D PET imaging data, 2-D X-ray imaging data, projection imaging data, fluoroscopy imaging data, CT imaging data, and MR imaging data.

DETAILED DESCRIPTION

Figure 1A:
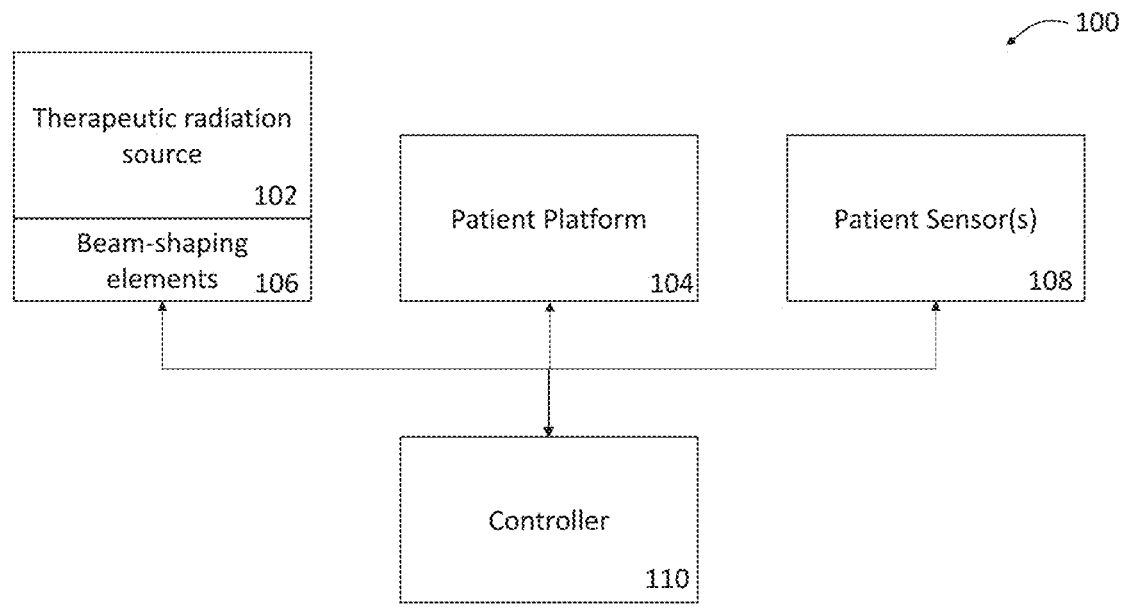
FIG. 1A depicts a flowchart representation of a radiotherapy system.

Disclosed herein are methods for radiotherapy treatment planning and radiation delivery using acquired target region sensor data. In some variations, sensor data may be acquired during a treatment session in the presence of a patient, while in other non-therapeutic variations, sensor data may be acquired during a QA session in the absence of a patient. A radiation therapy system may comprise one or more target region sensors (also referred to herein as target sensors) and the data acquired by the one or more target sensors during a radiation delivery (e.g., QA or treatment session) may be used to calculate the radiation fluence to be delivered to one or more target regions during the radiation delivery session. Target region sensors may comprise image sensors (e.g., X-ray detectors, PET detectors, and/or optical sensors, etc.), and/or may comprise position sensors that may be coupled to the patient and/or target region (e.g., a phantom and/or fluence measurement devices, such as an ion chamber and/or radiographic film). Radiotherapy treatment planning methods may comprise calculating, for each patient target region, shift-invariant firing filters based on a sensor characterization PDF of the one or more target sensors that are used during the treatment session. During the treatment session, readings from the target sensor(s) may be used to generate a sensor image, and the sensor image may be convolved with a shift-variant firing filter to calculate the delivery radiation fluence. The calculation of the delivery radiation fluence may occur within an hour (e.g., within about 60 minutes, within about 30 minutes, within about 20 minutes, within about 15 minutes, within about 10 minutes, within about 5 minutes, within about 3 minutes, within about 1 minute, within about 0.5 minute, within about 20 seconds, within about 2 seconds, within about 1 second, within about 0.5 second, within about 0.25 second, within about 0.2 second, within about 0.1 second, etc.) of emitting therapeutic radiation to the patient target region. In some variations, the one or more target sensors may comprise one or more position sensors that may be associated with different anatomical structures of the patient, and may, for example, comprise position sensors that sense the positions of one or more patient target regions, one or more organs-at-risk (OARs), and/or one or more bony structures that may be used by the radiotherapy system as anatomical landmarks and/or reference points for radiation delivery. Alternatively, or additionally, target sensors may comprise one or more image sensors, for example, an array of PET detectors, an array of MV detectors, an array of kV detectors, and/or an optical detector (e.g., a camera that detects visible light and/or infrared light). In these cases, the sensor data readings may already be an image, so no additional sensor data image generation may be needed. In some variations, a patient's position may be sensed by coupling a marker to the patient and using a camera to monitor the position and/or motion of the marker.

In some variations, radiotherapy treatment planning may use sensor characterization data from multiple target sensors to calculate multiple sets of corresponding firing filters. For example, a radiotherapy treatment planning method may comprise generating a first sensor characterization image based on a first sensor characterization PDF of a first target sensor, generating a second sensor characterization image based on a second sensor characterization PDF of a second target sensor, calculating a first set of firing filters that may be applied to sensor data from the first target sensor acquired during a treatment session, and calculating a second set of firing filters that may be applied to sensor data from the second target sensor acquired during a treatment session. The first target sensor and the second target sensor may be the same sensor type and/or may be different sensor types. During a treatment session, sensor data may be acquired from both the first target sensor and the second target sensor, used to generate first and second sensor data images, which are then convolved with their respective firing filters to generate a radiation fluence map for delivery.

While the examples provided herein are in the context of intensity modulated radiation therapy (IMRT), stereotactic body radiation therapy (SBRT), and/or biologically guided radiation therapy (BgRT), it should be understood that the systems and methods described herein may be used in any type of external beam radiation therapy. Moreover, while the some of the methods described herein are described in the context of a treatment session where radiation may be delivered to a patient, the same methods may be used in a quality assurance (QA) session that does not include radiation delivery to a patient. That is, the methods described herein may also be used in a non-therapeutic manner, such as in a QA procedure or session, where radiation is delivered to a phantom and/or fluence measurement devices instead of a patient. Accordingly, methods that are described as delivering radiation to a patient target region may also be used to deliver radiation to a target region of a phantom that is located in the patient area of a radiotherapy system. In some variations, the phantom may be anthropomorphic and/or may optionally be mounted on a motion simulator to mimic patient motion. Examples of fluence measurement devices may include, but are not limited to, ionization chamber(s), arrays of diodes and/or thin-film transistors (TFT), a thermoluminescent dosimeter (TLD), dosimeter, and the like.

Systems

FIG. 1A is a block diagram representation of an external beam radiation therapy system. Radiation therapy system (100) comprises one or more therapeutic radiation sources (102) and a patient platform (104). The therapeutic radiation source may comprise an X-ray source, electron source, proton source, and/or a neutron source. For example, a therapeutic radiation source (102) may comprise a linear accelerator (linac), Cobalt-60 source, and/or an X-ray machine. The therapeutic radiation source may be movable about the patient platform so that radiation beams may be directed to a patient on the patient platform from multiple firing positions and/or angles. In some variations, a radiation therapy system may comprise one or more beam-shaping elements and/or assemblies (106) that may be located in the beam path of the therapeutic radiation source. For example, a radiation therapy system may comprise a linac (102) and a beam-shaping assembly (106) disposed in a path of the radiation beam. The beam-shaping assembly may comprise one or more movable jaws and a multi-leaf collimator (e.g., a binary multi-leaf collimator, a 2-D multi-leaf collimator, etc.). The linac and the beam-shaping assembly may be mounted on a gantry that comprises a motion system configured to adjust the position of the linac and the beam-shaping assembly. The patient platform (104) may also be movable. For example, the patient platform (104) may be configured to translate a patient linearly along a single axis of motion (e.g., along the IEC-Y axis), and/or may be configured to move the patient along multiple axes of motion (e.g., 2 or more degrees of freedom, 3 or more degrees of freedom, 4 or more degrees of freedom, 5 or more degrees of freedom, etc.). In some variations, a radiation therapy system may have a 5-DOF patient platform that is configured to move along the IEC-Y axis, the IEC-X axis, the IEC-Z axis, as well as pitch and yaw.

In some variations, a radiation therapy system (100) may comprise one or more target region sensors (108). A target sensor may comprise an image sensor (e.g., X-ray detectors, PET detectors, MR coils, and/or optical sensors, etc.) and/or a positional sensor (e.g., implantable beacon, surface marker, etc.) and/or composite sensor (e.g., X-ray tracked implantable fiducial system). In some variations, a positional sensor or composite sensor may be implanted surgically into a tumor or target region using any minimally invasive method (e.g., percutaneous placement using a needle) and/or may be implanted into the patient's skin in proximity to the target region. A radiation therapy system may comprise a target sensor system that has a plurality of sensor elements and/or components. In some variations, a target sensor system may comprise an imaging system. For example, a BgRT system, such as an EGRT system that is configured to deliver radiation based on PET emission data, may have a target sensor system having one or more arrays of PET detectors (i.e., a PET imaging system). The PET emission data may be used to characterize the position of one or more patient tumors and/or the biological and/or physiological state of the patient. Alternatively, or additionally, a radiation therapy system may have a target sensor system that includes a CT imaging system. A CT imaging system may comprise an X-ray source (e.g., a kV X-ray source) and an X-ray detector located opposite the X-ray source. A radiopaque implantable fiducial may be placed at a predetermined patient region (e.g., using percutaneous methods, needle implantation, etc.), and the CT imaging system or an X-ray projector system may be configured to image and track the location of the fiducial. Optionally, a target sensor may comprise an X-ray detector (e.g., a MV X-ray detector) that is located opposite the therapeutic radiation source. The X-ray detector data may be used to characterize a position of a patient. One example of a target sensor system may comprise an injectable or implantable reflector that is less than about 1 cm that may be placed into a patient target region. The target sensor system may also comprise a detector that uses a radar signal that may be used to identify the location of the reflector. Alternatively, or additionally, a target sensor system may comprise an optical detector that is configured to sense light in the visible spectrum and/or near-infrared spectrum. For example, a target sensor system may comprise a camera that is positioned such that the patient platform is in its field of view, and the camera may be configured to acquire a video stream (e.g., a series of images over time) from which the location and/or motion of the patient may be determined. Optionally, to facilitate the detection of a patient's location and/or motion, a marker, tag, optical fiducial, and/or any visual indicia may be coupled to the patient that may facilitate the detection of the patient's position and/or motion by the camera. For example, an optical fiducial may be coupled to a patient's skin, using an adhesive and/or strap. In some variations, the marker or tag may comprise an optical emitter (e.g., emitting light of a preselected wavelength and/or pulse frequency) and the camera may be configured to detect the light from the emitter. Alternatively, or additionally, a marker or tag may be an object that has optical properties that may be distinctive from the ambient optical environment. For example, a marker, tag, or other such optical fiducial may have a unique solid color, distinctive visual patterns, high-contrast markings, and/or high-optical reflectivity characteristics that may facilitate detection by an image processor of the camera. That is, the marker or tag may comprise visually distinctive patterns or graphics that allow it to be easily distinguished from background features. In some variations, the marker or tag may be a pigment that is injected into a local region of the patient's skin (e.g., a tattoo). The pigment may comprise a radiopaque material that may be detected using an X-ray (e.g., CT) imaging system.

In some variations, a target sensor may comprise a position sensor that is configured or arranged to detect the location and/or motion of the patient. In some variations, at least one position sensor may be attached to an anatomical structure in proximity to a target region (e.g., a tumor or lesion), and/or an anatomical structure whose location and/or movement may be correlated with the location and/or movement of the target region.

Some variations of a radiation therapy system may comprise one or more target sensors of different sensing modalities. For example, a radiation therapy system may have a target sensor system that comprises an imaging system (e.g., PET imaging system, CT imaging system, MR imaging system, optical or visible light imaging system, fluoroscopy imaging system) and a target sensor that comprises a position sensor that may be attached to the patient during a treatment session. A radiation therapy system may have a first target sensor system comprising a CT imaging system (i.e., a kV X-ray source and detector, X-ray projector system), a second target sensor system comprising a PET imaging system (i.e., a plurality of PET arrays arranged in a continuous ring or in two separate opposing arcs), and/or a third target sensor system comprising the therapeutic radiation source and the MV detector located opposite the therapeutic radiation source. Radiation therapy systems may comprise a first target sensor system comprising a CT imaging system and a second target sensor comprising a position sensor coupled to the patient at a location that is correlated with the location of a patient target region. Alternatively, or additionally, a radiation therapy system may have a plurality of position sensors that are attached to predetermined regions of a patient's body that may be provide additional information about the location of a patient target region.

While the description herein describes target sensors in the context of radiation delivery to a patient, it should be understood that the target sensor may also include sensors in the context of radiation delivery during a non-therapeutic procedure (e.g., a QA procedure or session) in the absence of a patient. The target sensors described above may also be used in a QA procedure or session for radiation delivery to a phantom and/or fluence measurement device; that is, the target sensors and/or sensor systems may also be used in a non-therapeutic procedure that does not involve radiation delivery to a patient. The various functions, structures, and systems of target sensors and/or sensor systems as described herein may be used during a QA procedure or session where the patient is replaced by a phantom. For example, a target sensor system may comprise an imaging system (e.g., PET imaging system, CT imaging system, MR imaging system, optical or visible light imaging system, fluoroscopy imaging system) may be used in a QA procedure where radiation is delivered to a phantom instead of a patient. A position sensor, a marker, tag, optical fiducial, and/or any visual indicia may be applied to a phantom as it would be applied to a patient. Any of the target sensors described herein (e.g., image sensor, and/or a positional sensor, and/or composite sensor, etc.) may be used with a phantom and/or fluence measurement device during a non-therapeutic procedure.

A radiation therapy system (100) also comprises a controller (110) that is in communication with the therapeutic radiation source (102), the beam-shaping elements or assemblies (106), the patient platform (104), and the one or more target sensors (108) (e.g., one or more target sensor systems). The controller (110) may comprise one or more processors and one or more machine-readable memories in communication with the one or more processors, which may be configured to execute or perform any of the methods described herein. The one or more machine-readable memories may store instructions to cause the processor to execute modules, processes and/or functions associated with the system, such as one or more treatment plans, target sensor data (e.g., imaging data, location/position data, motion data), the calculation of radiation fluence maps based on treatment plan and/or clinical goals, segmentation of fluence maps into radiation therapy system instructions (e.g., that may direct the operation of the gantry, therapeutic radiation source, beam-shaping assembly, patient platform, and/or any other components of a radiation therapy system), and image and/or data processing associated with treatment planning and/or radiation delivery. In some variations, the memory may store treatment plan data (e.g., treatment plan firing filters, fluence map, planning images), target sensor data, instructions for processing the sensor data to derive a radiation delivery fluence map, and instructions for delivering the derived fluence map (e.g., instructions for operating the therapeutic radiation source, beam-shaping assembly and patient platform in concert). The controller of a radiation therapy system may be connected to other systems by wired or wireless communication channels. For example, the radiation therapy system controller may be in wired or wireless communication with a radiotherapy treatment planning system controller such that fluence maps, firing filters, target sensor data (e.g., a sensor characterization probability density function), planning images (e.g., CT images, MRI images, PET images, 4-D CT images), patient data, and other clinically-relevant information may be transferred from the radiotherapy treatment planning system to the radiation therapy system. The delivered radiation fluence, any dose calculations, and any clinically-relevant information and/or data acquired during the treatment session may be transferred from the radiation therapy system to the radiotherapy treatment planning system. This information may be used by the radiotherapy treatment planning system for adapting the treatment plan and/or adjusting delivery of radiation for a successive treatment session.

Figure 1B:
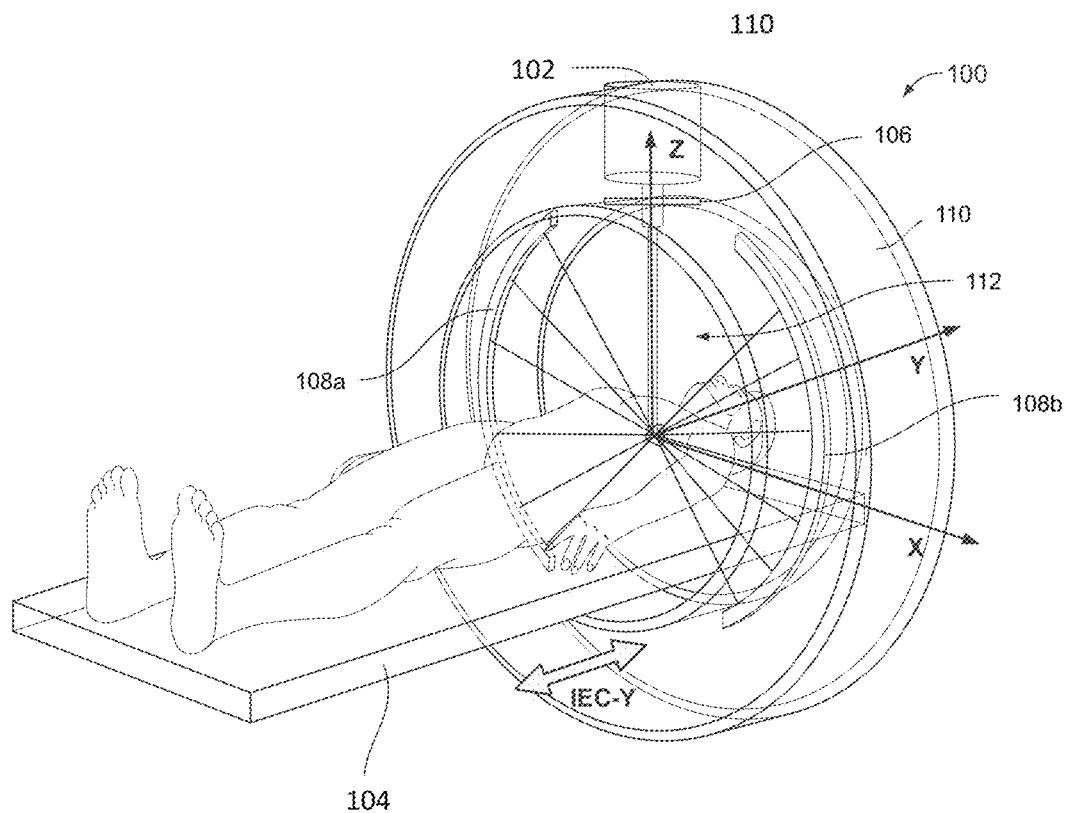
FIGS. 1B-1C depict one variation of a radiotherapy system.

FIG. 1B depicts one variation of a radiation therapy system (100). Radiation therapy system (100) may comprise a gantry (110) rotatable about a patient treatment region (112), one or more PET detectors (108) mounted on the gantry, a therapeutic radiation source (102) mounted on the gantry, a beam-shaping module (106) disposed in the beam path of the therapeutic radiation source, and a patient platform (119) movable within the patient treatment region (112). In some variations, the gantry (110) may be a continuously-rotating gantry (e.g., able to rotate through 3600 and/or in arcs with an angular spread of less than about 360°). The gantry (110) may be configured to rotate from about 20 RPM to about 70 RPM about the patient treatment region (112). For example, the gantry (110) may be configured to rotate at about 60 RPM. The beam-shaping module (106) may comprise a movable jaw and a dynamic multi-leaf collimator (MLC). The beam-shaping module may be arranged to provide variable collimation width in the longitudinal direction of 1 cm, 2 cm or 3 cm at the system iso-center (e.g., a center of a patient treatment region). The jaw may be located between the therapeutic radiation source and the MLC or may be located below the MLC. Alternatively, the beam-shaping module may comprise a split jaw where a first portion of the jaw is located between the therapeutic radiation source and the MLC, and a second portion of the jaw is located below the MLC and coupled to the first portion of the jaw such that both portions move together. The therapeutic radiation source (102) may be configured to emit radiation at predetermined firing positions (e.g., firing angles 0°/360° to 359°) about the patient treatment region (112). For example, in a system with a continuously-rotatable gantry, there may be from about 50 to about 100 firing positions (e.g., 50 firing positions, 60 firing positions, 80 firing positions, 90 firing positions, 100 firing positions, etc.) at various angular positions (e.g., firing angles) along a circle circumscribed by the therapeutic radiation source as it rotates. The firing positions may be evenly distributed such that the angular displacement between each firing position is the same.

Figure 1C:
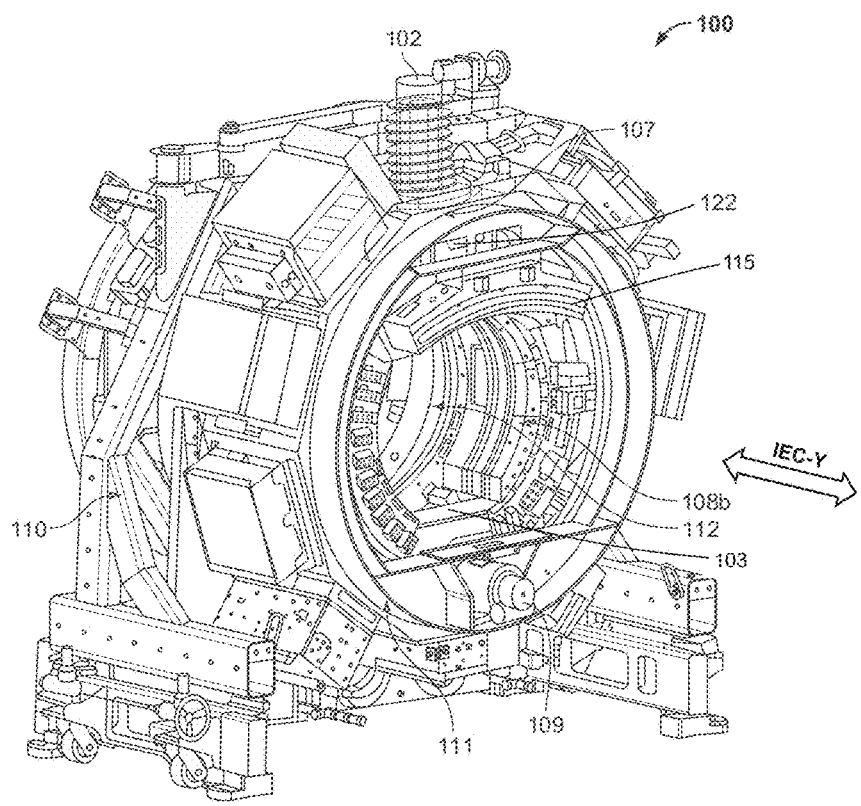

FIG. 1C is a perspective component view of the radiation therapy system (100). As shown there, the beam-shaping module may further comprise a primary collimator or jaw (107) disposed above the binary MLC (122). The radiation therapy system may also comprise an MV X-ray detector (103) located opposite the therapeutic radiation source (102). Optionally, the radiation therapy system (100) may further comprise a kV CT imaging system on a rotatable ring (111) that is attached to the rotatable gantry (110) such that rotating the gantry (110) also rotates the ring (111). The kV CT imaging system may comprise a kV X-ray source (109) and an X-ray detector (115) located across from the X-ray source (109). The therapeutic radiation source or linac (102) and the PET detectors (108) may be mounted on the same cross-sectional plane of the gantry (i.e., PET detectors are co-planar with a treatment plane defined by the linac and the beam-shaping module), while the kV CT scanner and ring may be mounted on a different cross-sectional plane (i.e., not co-planar with the treatment plane). The radiation therapy system (100) of FIGS. 1B and 1C may have a first target sensor system that comprises the kV CT imaging system and a second target sensor system that comprises the PET detectors. Optionally, a third target sensor system may comprise the MV X-ray source and MV detector. The target sensor data acquired by one or more of these target sensor systems may include X-ray and/or PET imaging data, and the radiation therapy system controller may be configured to store the acquired target sensor data and calculate a radiation delivery fluence using the target sensor data. In some variations, additional target sensors, such as position sensors, may be included, and the controller may be configured to receive location and/or motion data from the position sensor and incorporate this data with other target sensor data to calculate a radiation delivery fluence. Additional descriptions of radiotherapy systems that may be used with any of the methods described herein are provided in U.S. Pat. No. 10,695,586, filed Nov. 15, 2017.

The patient platform (104) may be movable in the treatment region (112) to discrete, pre-determined locations along IEC-Y. These discrete, pre-determined locations may be referred to as "beam stations". For example, a radiotherapy treatment planning system may specify 200 beam stations, where each beam station is about 2 mm (e.g., 2.1 mm) apart from its adjacent beam stations. The number of beam stations may vary from about 50 to about 500, and the spacing between each beam station may be at least about 0.5 mm (e.g., about 1 mm or more, about 2 mm or more, about 20 mm or more, about 50 mm or more, etc.). During a treatment session, the radiotherapy treatment system may move the patient platform to each of the beam stations and may stop the platform at a beam station while radiation is delivered to the patient. In some variations, after the platform has been stepped to each of the 200 beam stations in a first direction (e.g., into the bore), the platform may be stepped to each of the 200 beam stations in a second direction opposite the first direction (e.g., out of the bore, in reverse), where radiation is delivered to the patient while the platform is stopped at a beam station. Alternatively, or additionally, after the platform has been stepped to each of the 200 beam stations in a first direction (e.g., into the bore) where radiation is delivered at each of the beam stations, the platform may be moved in reverse so that it returns to the first beam station. No radiation may be delivered while the platform is moved back to the first beam station. The platform may then be stepped, for a second time, to each of the 200 beam stations in the first direction for a second pass of radiation delivery. In some variations, the platform may be moved continuously while radiation is delivered to the patient and may not be stopped at beam stations. Additional descriptions of patient platforms that may be used with any of the radiotherapy systems and methods described herein are provided in U.S. Pat. No. 10,702,715, filed Nov. 15, 2017.

Figure 1D:
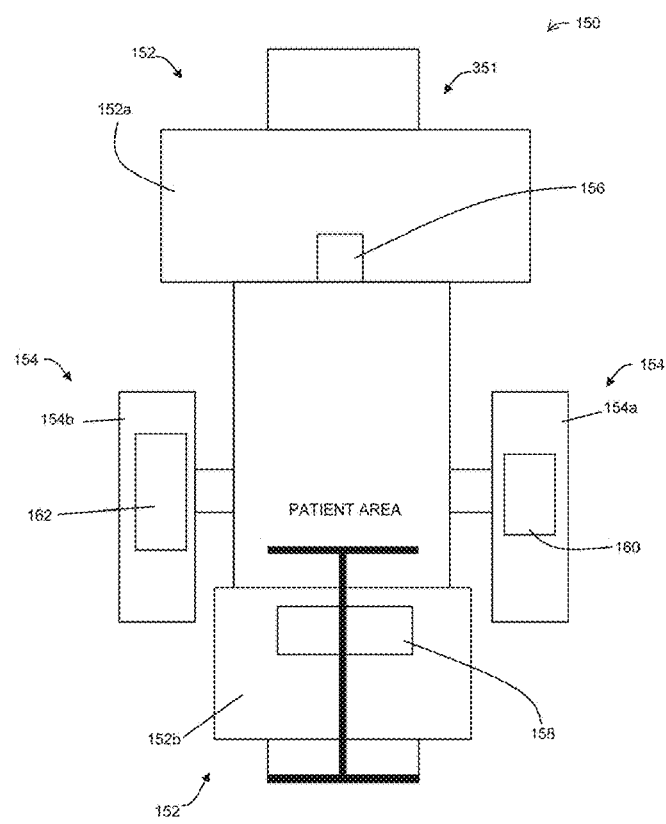
FIG. 1D depicts a variation of a radiotherapy system.

FIG. 1D depicts another variation of a radiation therapy system (150) that may be used to deliver radiation in accordance with any of the methods described herein. The radiation therapy system (150) may have the components of the radiation therapy system represented in the block diagram of FIG. 1A. Radiation therapy system (150) may comprise a gantry (151) comprising a first pair of arms (152) rotatable about a patient area and a second pair of arms (154) rotatable about the patient area, an imaging system comprising a therapeutic radiation system comprising an MV radiation source (156) mounted on a first arm (152a) of the first pair of arms (152) and an MV detector (158) mounted on a second arm (152b) of the first pair of arms (152), and a kV radiation source (160) mounted on a first arm (154a)

of the second pair of arms (154) and a kV detector (162) mounted on a second arm (154b) of the second pair of arms (154). The first and second arms of the first pair of arms (152) may be located opposite each other (e.g., on opposite sides of the patient area, across from each other, and/or about 180 degrees from each other), such that the MV radiation source (156) and the MV detector (158) are located opposite each other (e.g., the MV detector is located in the beam path of the MV radiation source). The first and second arms of the second pair of arms (154) may be located opposite each other (e.g., on opposite sides of the patient area, across from each other, and/or about 180 degrees from each other), such that the kV radiation source (160) and the kV detector (162) are located opposite each other (e.g., the kV detector is located in the beam path of the kV radiation source). In this system, the target sensor system may comprise the kV radiation source and kV detector. Optionally, a second target sensor system may comprise the MV radiation source and the MV detector. Target sensor data may comprise imaging data acquired by the kV detector (and/or MV detector) after each kV X-ray source (and/or MV X-ray source) pulse. Examples of target sensor data may include X-ray projection imaging data, such as 2D projection data. The radiation therapy system controller may be configured to store the acquired target sensor data and calculate a radiation delivery fluence using the target sensor data. In some variations, additional target sensors, such as position sensors, may be included, and the controller may be configured to receive location and/or motion data from the position sensor and incorporate this data with other target sensor data to calculate a radiation delivery fluence.

The MV radiation source (156) (i.e., the therapeutic radiation source) may be configured to emit radiation at predetermined firing positions about the patient area. In some variations where the MV radiation source is moved around the patient area along a single plane, the firing positions may be referred to as firing angles, which may be from 0°/360° to 359°. Alternatively or additionally, the gantry and/or gantry arms may be configured to move the MV radiation source to a firing position at any coordinate(s) in 3-D space, i.e., as designated by coordinates (x,y,z). For example, the gantry arms (152, 154) may be robotic arms having articulated joints that may be configured to position and/or orient the MV radiation source at any desired firing position. The gantry may be configured to continuously move MV radiation source through the firing positions or may be configured to step the MV radiation source to each firing position (i.e., move the MV radiation source to a firing position and remain stationary at that firing position). Alternatively, or additionally, the MV radiation source may be configured to emit radiation only at the predetermined firing positions or may be configured to emit radiation continuously, even as it is being moved from one firing position to the next.

Radiotherapy Treatment Planning Methods

The target sensors and/or target sensor systems may be configured to provide a continuous stream of sensor data in real-time during a radiation delivery session (e.g., a treatment session or QA session). The controller or a radiation therapy system may be configured to calculate a radiation fluence map based on this target sensor data and to deliver the calculated radiation fluence on the same day in which the sensor data was acquired, for example, within hours of acquiring target sensor data (e.g., less than about 2 hours, less than about 1 hour, etc.), within minutes of acquiring target sensor data (e.g., less than about 45 minutes, less than about 30 minutes, less than about 15 minutes, less than about 5 minutes, less than about 3 minutes, etc.), and/or within seconds of acquiring the target sensor data (e.g., less than about 5 seconds, less than about 3 seconds, less than about 2 seconds, less than about 1 second, less than about 0.5 seconds, less than about 250 ms, less than about 100 ms, etc.). The controller may be configured to continuously acquire target sensor data in specified time windows from about 0.1 seconds to about 10 minutes. In some variations, the controller may be configured to continuously acquire target sensor data in short time windows (e.g., about 2 seconds or less, about 1 second or less, about 0.5 second or less, etc.), and to use the target sensor data acquired during a short time window to calculate the radiation to be delivered within the subsequent delivery window (e.g., which may be similarly short as the acquisition time window). For example, the sensor data acquisition time window may be approximately proportional to the delivery window. In some variations, a delivery window is the interval of time where the calculated radiation is to be delivered. For example, in a radiotherapy system where the therapeutic radiation source is continuously rotating about a patient area where the dwell time per firing position/angle is about 10 ms, a delivery window may be 100 ms, during which time the therapeutic radiation source would have emitted radiation pulses at 10 firing positions/angles. However, sensor data acquired within a short period of time may be noisy (e.g., have low signal-to-noise ratios) and/or may not contain much information about a patient target region. For example, PET and/or X-ray imaging data acquired over a 0.5 second window of time may not be adequate to generate an image with sufficient resolution to identify the location of the patient target region. However, if the noise characteristics and/or the variabilities of the target sensors are known in advance of a treatment session, this information may be incorporated into the treatment plan. The radiotherapy treatment planning methods described herein may comprise calculating firing filters that incorporate the noise characteristics and/or sensor variabilities (e.g., sensor probability density functions) of the one or more target sensors that are activated during a treatment session (or any radiation delivery session, including a QA session). The calculated firing filters may be applied to the target sensor data acquired during a treatment session. This may facilitate the delivery of therapeutic radiation to a moving patient target region despite any noisy and/or incomplete target sensor data. Similarly, target sensors may be used in a QA session where the patient is replaced by a phantom, which may include a region that simulates the location and/or properties of a patient target region. In some variations, the phantom may be mounted on a motion stage to simulate motion of the patient target region during an actual treatment session. The motion may be based, in some variations, on a motion dwell histogram for the target region. The calculated firing filters may be applied to the target sensor data acquired during the QA session to deliver radiation to the target region. Measurements of the delivered radiation to the phantom target region may facilitate the evaluation of the treatment plan and function of the radiotherapy system. In some variations, the data acquired during a QA session from the target sensors may be used to modify the treatment plan and/or adjust components of the radiotherapy system.

The radiotherapy treatment planning methods described herein may comprise generating a set of shift-invariant firing filters for each target sensor modality. The shift-invariant firing filters may be linear functions or operators, or may be non-linear functions or operators. For example, if a single position sensor will be used to acquire real-time patient position data (e.g., location and/or motion data) during a treatment session, the treatment planning system may use the position sensor's characterization data converted to an image to calculate a set of firing filters. A position sensor's characterization data may comprise a sensor error PDF. During a treatment session, the calculated firing filters may be applied to position sensor data images (that are generated based on position sensor data acquired in real-time) to calculate the radiation fluence map for delivery. In some variations, the position sensor data image may be a discrete 3-D delta function that is centered over a position sensor data reading, a discretized Gaussian function image with mean centered at the position sensor data reading, a truncated Gaussian function, etc. In another example, if image sensors for a single imaging modality (e.g., kV detectors, PET detectors, MV detectors, etc.) will be used to acquire real-time patient and/or patient target region position data (e.g., location and/or motion data) during a treatment session, the treatment planning system may use a planning image generated by the same image sensors (and/or generated in the same imaging modality), which may be low-noise and non-sparse, as a PDF to calculate a set of firing filters. During a treatment session, the calculated firing filters may be applied to image sensor data acquired in real-time (which may be noisy or sparse) to calculate the radiation fluence map for delivery. In one variation, two or more different target sensor modalities may be used during a treatment session to acquire real-time patient and/or patient target region position data (e.g., location and/or motion data) during a treatment session. For example, a radiation therapy system may comprise an imaging system comprising one or more image sensors (e.g., PET detectors, X-ray detectors) that are configured to acquire imaging data during a treatment session. In addition, a position sensor may be coupled to the patient and configured to acquire location and/or motion data during the treatment session. The treatment planning system may use a planning image generated by the same one or more image sensors (and/or generated in the same imaging modality) as a PDF to calculate a first set of firing filters and use the position sensor's error PDF converted to an image (e.g., a sensor characterization image) to calculate a second set of firing filters. During the treatment session, to calculate the delivery fluence, the controller may apply the first set of firing filters to the real-time acquired imaging data, apply the second set of firing filters to the real-time acquired position data (i.e., position sensor data image(s) generated from the acquired position data), and combine them together to calculate a radiation fluence map for delivery. Any combination of target sensor modalities may be used during a treatment session to acquire data about the patient and/or one or more patient target regions (e.g., location, motion, and/or biological and/or physiological state of the patient and/or target regions). Accordingly, a radiotherapy treatment planning method may comprise calculating a set of firing filters for each of the target sensor modalities. During the treatment session, the firing filters may be applied to their respective target sensor data and then combined to calculate the radiation fluence map for delivery.

The methods for generating treatment plans described herein are carried out in the absence of a patient. These treatment planning methods alone do not include the delivery of therapeutic radiation to a patient.

Radiotherapy Treatment Planning Method: Single Sensor

Figure 2A:
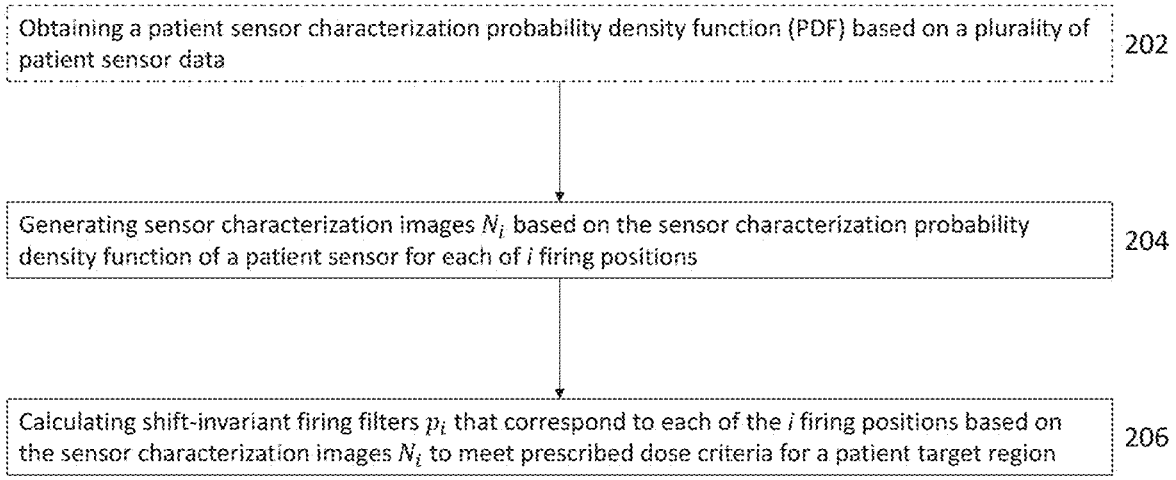
FIG. 2A depicts a flowchart representation of a treatment planning method using data from a sensor.
Figure 2B:
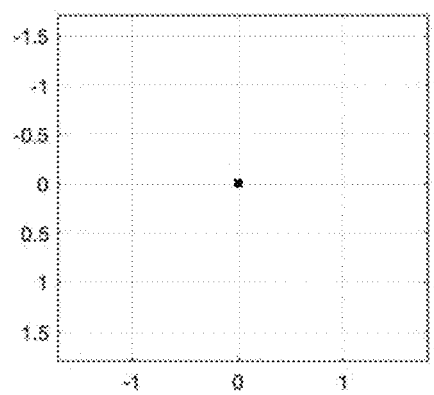
FIG. 2B depicts a sensor image of a position sensor data reading.

One variation of a radiotherapy treatment planning method that incorporates target sensor data from a target sensor is depicted in FIG. 2A. Method (200) may comprise obtaining (202) the target sensor characterization PDF, generating (204) target sensor characterization images $N_i$ that are based on the sensor characterization PDF of a target sensor for each firing position i of the therapeutic radiation source, and calculating (206) shift-invariant firing filters that correspond to each of the i firing positions based on the target sensor characterization images $N_i$ and prescribed dose criteria for a patient target region. In some variations, the target sensor characterization PDF may be provided by previous models and/or calculations, in which case, obtaining (202) the sensor characterization PDF may be optional. A sensor characterization PDF may be a sensor error PDF. The sensor characterization PDF may be derived from a plurality of target sensor data. That is, $$M = \sum_{j=1}^{k} m_j$$

where $m_j$ is a sensor data reading converted to an image and M is an image of the sensor characterization PDF, which is the summation of k sensor data readings. For example, the sensor characterization PDF of a position sensor (which may be a sensor error PDF) may comprise a histogram of position sensor data readings or sensor errors. Position sensor data readings may be one dimensional (1-D; location is designated by a single coordinate x), two dimensional (2-D; location is designated by two coordinates x and y), and/or three dimensional (3-D; location is designated by three coordinates x, y, and z). In some variations, position sensor data readings may be changes or deviations in location relative to an initial or baseline location. Additionally, or alternatively, the sensor characterization PDF histogram may represent position sensor data variability. That is, for a "true" position value, the position sensor data readings may be different due to sensor noise and/or other variabilities. The sensor characterization PDF may be an accumulation of the position sensor data or error readings over a period of time.

Figure 2C:
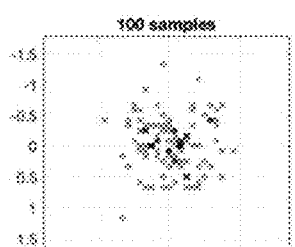
FIGS. 2C-2K depict sensor error images of a position sensor.
Figure 2D:
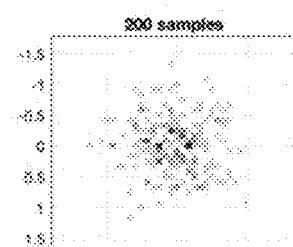
Figure 2E:
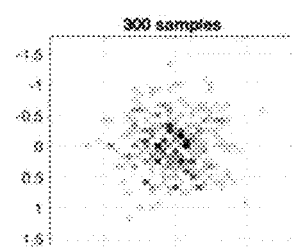
Figure 2F:
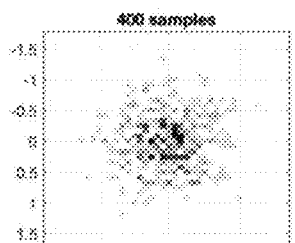
Figure 2G:
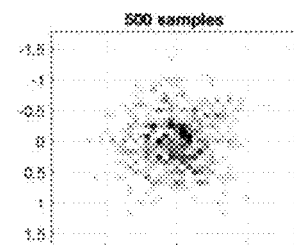
Figure 2H:
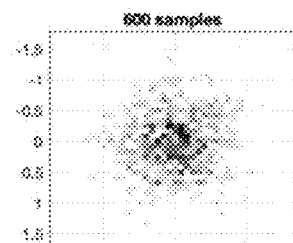
Figure 2I:
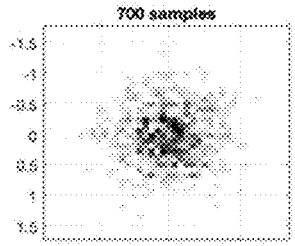
Figure 2J:
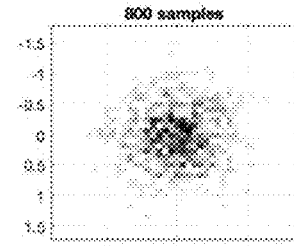
Figure 2K:
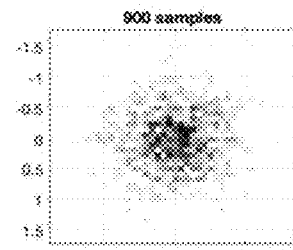
Figure 2L:
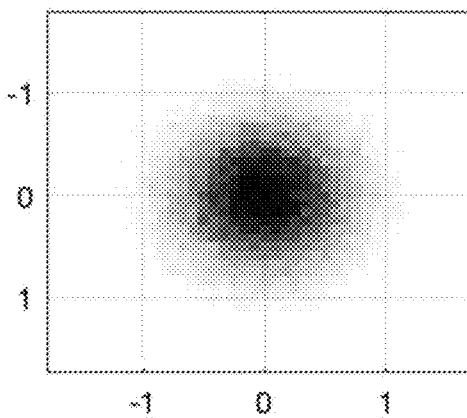
FIG. 2L depicts a sensor characterization image of the sensor error characterization probability distribution function of a position sensor.

FIG. 2L is an example of an image of a position sensor characterization PDF. FIGS. 2B-2K depict one example of how the sensor characterization PDF image of FIG. 2L may be generated (204). A position sensor data reading may be, for example, two coordinate values (x,y). This position data reading may convert into an image or plot. For example, a position data sensor reading of (0,0) may be converted into the sensor image depicted in FIG. 2B, which is a plot of a delta function centered around (0,0). Alternatively, the position data sensor reading (0,0) may be converted to a gaussian function centered around (0,0); that is, a gaussian function or truncated gaussian function centered at the "true" value, having a FWHM that is calculated based on the resolution of the position sensor and/or the resolution (e.g., granularity) with which the radiation therapy system can precisely deliver a radiation beam. Additional position data sensor readings may be acquired, and the sensor characterization PDF may be a list of position data sensor readings. The sensor characterization PDF may be a histogram derived from the list of position data sensor readings. Method (200) comprises generating an image of the sensor characterization PDF, and in this example, this may comprise plotting the error (or difference) of each of the position sensor readings as compared to the position sensor reading represented in FIG. 2B (which is centered at (0,0)): FIG. 2C is a sensor error image of the error (or difference) of 100 position data sensor readings as compared to the reading at (0,0), FIG. 2D is a sensor error image of the error of 200 position sensor readings as compared to the reading at (0,0), FIG. 2E is a sensor error image of the error of 300 position sensor readings as compared to the reading at (0,0), FIG. 2F is a sensor error image of the error of 400 position sensor readings as compared to the reading at (0,0), FIG. 2G is a sensor error image of the error of 500 position sensor readings as compared to the reading at (0,0), FIG. 2H is a sensor error image of the error of 600 position sensor readings as compared to the reading at (0,0), FIG. 2I is a sensor error image of the error of 700 position sensor readings as compared to the reading at (0,0), FIG. 2J is a sensor error image of the error of 800 position sensor readings as compared to the reading at (0,0), and FIG. 2K is a sensor error image of the error of 900 position sensor readings as compared to the reading at (0,0). As more position sensor readings are acquired, each translated to a delta function and aggregated, a sensor image of the sensor error characterization PDF (e.g., FIG. 2L) may be generated. A similar method may be used to generate position sensor error characterization PDFs for 1-D or 3-D sensor readings. Conceptually, the sensor error characterization PDF image depicted in FIG. 2L may represent the variability of the sensor for a "true" position value at (0,0), i.e., a sensor error characterization PDF. That is, when an object is located at (0,0), the position sensor may provide a data reading that is not (0,0), and the probability that the position sensor may provide any particular data reading value is in accordance with the density of that data value in the FIG. 2L sensor error characterization PDF image. In this example, there is a greater likelihood that the position sensor will output a data reading value that is close to the "true" position value (i.e., densest portion of the image is around (0,0)), than the likelihood that the position will output a data reading value that is at the outer edge of the error PDF (i.e., the outer edges are least dense). In some variations, the image of the sensor characterization PDF may be a gaussian "ball" if the sensor errors/variabilities are normally distributed.

Figure 3A:
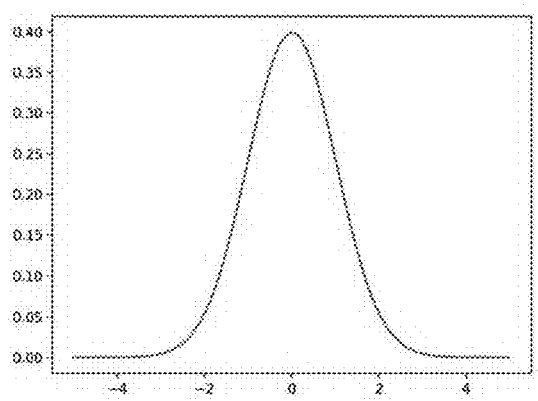
FIGS. 3A-3E depict variations of sensor images.
Figure 3B:
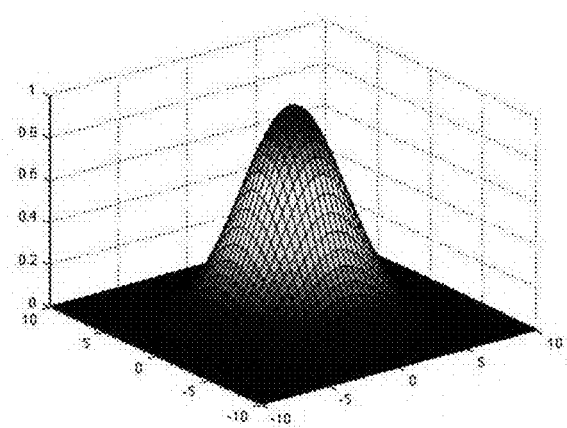
Figure 3C:
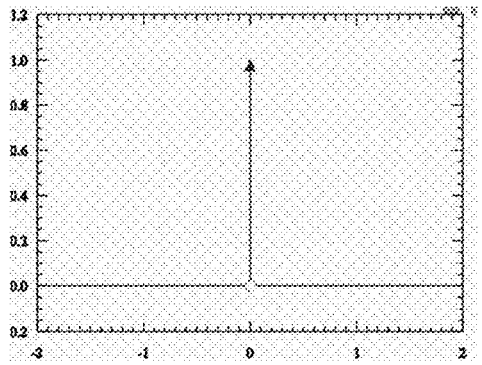
Figure 3D:
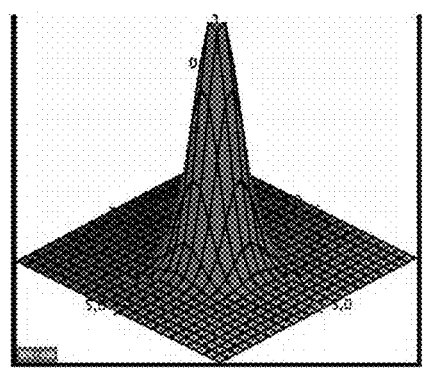
Figure 3E:
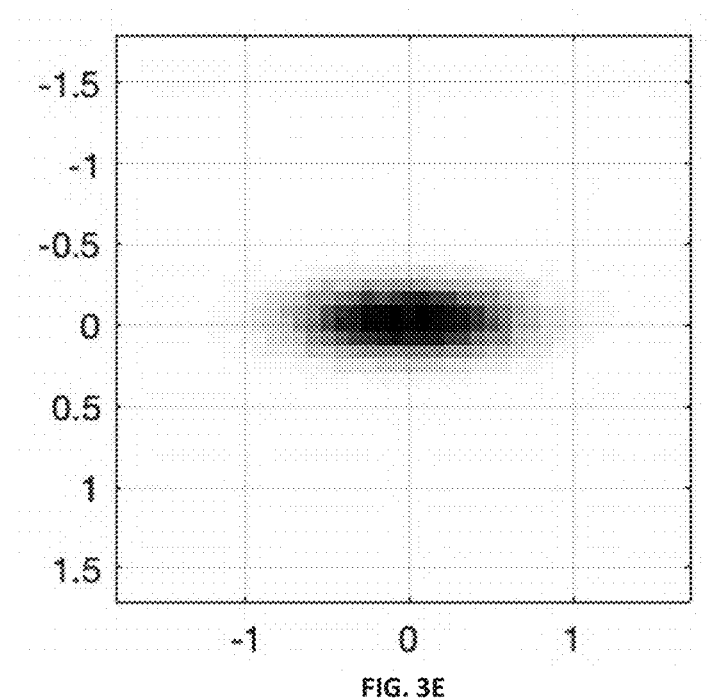

FIGS. 3A-3E depict examples of various sensor images. In some variations, a sensor image may be a 2-D Gaussian function (FIG. 3A), 3-D Gaussian function (FIG. 3B) or a 3-D truncated Gaussian function (FIG. 3D). A sensor image may be a 2-D delta function (FIG. 3C), or a 3-D delta function. Some target sensors may have asymmetrical noise. FIG. 3E depicts one example of an image of a sensor characterization PDF of a target sensor with asymmetrical noise and/or errors and/or variability.

An image of the sensor characterization PDF (N) may be generated for each of i firing positions of the radiation therapy system. For example, a therapeutic radiation source may have 100 firing positions that represent different locations (which may be predetermined) from which it may emit radiation beam(s) to the patient. Generating (204) sensor characterization images $N_i$ may comprise calculating a projection of a sensor characterization PDF image N (e.g., the sensor error characterization PDF image of FIG. 2L) on each of the i firing positions, such that sensor characterization image $N_1$ is a projection of sensor characterization image N on firing position 1, sensor image $N_2$ is a projection of sensor characterization image N on firing position 2, and so forth, for each firing position. Alternatively, an image of the sensor characterization PDF can be calculated directly at each firing position using the beams eye-view space at that firing position.

A firing filter $p_i$ for firing position i may represent the relationship between a radiation fluence map $F_i$ for delivery at firing position i to a patient target region, and a target sensor characterization image $N_i$, such that $F_i = p_i * N_i$ (e.g., firing filter convolved with the sensor characterization PDF image).

In some variations, a firing filter may be a matrix $P_i$ that may be used to convert an image of target sensor characterization images $N_i$ into a radiation fluence $F_i$ (e.g., fluence map) for delivery, using matrix multiplication, in which case the sensor characterization image may be linearized into a vector. That is:

$F_i = P_i \cdot N_i$ (firing matrix is multiplied with vectorized sensor characterization image).

While a firing filter may be a linear function or operator in the examples described herein, in some variations, a firing filter may be a non-linear function or operator (e.g., a truncated convolution function, a convolution followed by a thresholding, matrix multiplication with a soft-max operator). Alternatively, or additionally, an image of target sensor data may be pre-processed (e.g., using one or more non-linear functions) before it is converted into a radiation fluence for delivery using a linear firing filter (e.g., a shift-invariant, linear firing filter).

The radiation fluence F (e.g., fluence map) over multiple firing positions (e.g., i number of firing positions) may be represented by:

$$F = \begin{bmatrix} p_0 * N_0 \\ \vdots \\ p_{i-1} * N_{i-1} \end{bmatrix}$$

For example, the radiation fluence for 50 firing positions may be:

$$F = \begin{bmatrix} p_0 * N_0 \\ \vdots \\ p_{49} * N_{49} \end{bmatrix}$$

During radiotherapy treatment planning, a clinician may provide a dose prescription for a patient target region and/or organ-at-risk (OAR). The dose prescription may include, for example, dose goals and objectives for a patient target region and/or OAR. Radiation dose (i.e., the amount of radiation absorbed by a subject) and radiation fluence (i.e., the amount of radiation emitted by a radiation source, and usually designated by radiation beams or beamlets) are related to each other (e.g., mapped to each other) by a dose calculation matrix A. That is, $D = A \cdot F$ A dose calculation matrix represents a dose contribution from each of a plurality of radiation beamlet to each voxel of a patient target region (and/or OAR). For example, a dose calculation matrix A may be a (k×n) matrix where n may be a number of possible radiation beamlets $\{b_i\}$ and k may be the number of pre-selected voxels for a patient target region. An i-th column of the dose calculation matrix A (which has k elements) represents a dose contribution from a unity-weighted beamlet $b_i$ to each of the k voxels. Dose calculation matrix A may be calculated column-by-column, for example, by ray-tracing each beamlet's aperture along the path through a patient target region and calculating the contribution of a unity-weighted beamlet to each of the k voxels. A beamlet aperture may be an MLC aperture defined by a single MLC leaf opening (i.e., of a binary MLC or a 2-D MLC). Examples of algorithms for calculating a dose calculation matrix that may be used in any of the methods described herein may include Monte-Carlo simulation, collapsed-cone convolution superposition, pencil-beam convolution, and others. Each patient target region and/or OAR may have its own dose calculation matrix.

As described above, radiation fluence map F may be represented by a firing filter p convolved with a target sensor characterization image N (F=p*N). Accordingly, $$D = A \cdot F = A \cdot (p*N)$$

where A is a dose calculation matrix. The cumulative dose over i firing positions may be:

$$D = A \cdot \begin{bmatrix} p_0 * N_0 \\ \vdots \\ p_{i-1} * N_{i-1} \end{bmatrix}$$

where $p_0 \ldots p_{i-1}$ are the firing filters and $N_0 \ldots N_{i-1}$ are the projections of a target sensor characterization image onto each of i firing positions.

In addition to defining a dose prescription, a clinician may set one or more constraints and/or cost or penalty functions C(D, F) that specify characteristics of the dose distribution and/or radiation fluence map. Examples of cost functions may include, but are not limited to, minimum dose to target region, average or maximum dose on OARs, and/or fluence smoothness, total radiation output, total tissue dose, treatment time, etc.

A radiotherapy treatment planning system may be configured to calculate a radiation fluence map F such that the dose prescription and constraints C(D, F) are met. The radiotherapy treatment planning system may iterate through different radiation fluence values and/or maps to find the fluence values and/or maps that minimize the cost function C(D, F) while still meeting the dose prescription requirements. To calculate (206) firing filters (e.g., shift-invariant firing filters) in accordance with method (200), a radiotherapy treatment planning system may set up an optimization problem for minimizing the cost function C(D, F), given a dose calculation matrix A and target sensor characterization images N. Calculating firing filters p may comprise iterating through different firing filter values such that the cost function C(D, F) is minimized while still attaining dose goals and objectives in accordance with the dose prescription:

$$D = A \cdot \begin{bmatrix} p_0 * N_0 \\ \vdots \\ p_{i-1} * N_{i-1} \end{bmatrix}$$

In some variations, the optimization problem above may be re-cast by converting the convolution of a firing filter with a target sensor characterization image into a matrix multiplication:

$$D = A \cdot \begin{bmatrix} N_0 * p_0 \\ \vdots \\ N_{i-1} * p_{i-1} \end{bmatrix} = A \cdot \begin{bmatrix} toep(N_0) & & \\ & \ddots & \\ & & toep(N_{i-1}) \end{bmatrix} \cdot \begin{bmatrix} p_0 \\ \vdots \\ p_{i-1} \end{bmatrix}$$

where the convolution of target sensor characterization images with firing filters has been converted to a matrix multiplication between a block diagonal of Toeplitz matrices of the target sensor characterization images and a column vector of firing filters for each firing position. Setting up the optimization problem using Toeplitz matrices results in firing filters that are shift-invariant convolutions. Since the dose calculation matrix A and the target sensor characterization images $N_i$ are known (i.e., previously calculated based on treatment planning images, target sensor data, target sensor PDF, target sensor error PDF, etc.), they may be combined into a single matrix, denoted $A^{GIGRT}$:

$$D = A^{GIGRT} \cdot \begin{bmatrix} p_0 \\ \vdots \\ p_{i-1} \end{bmatrix}$$

By grouping the known quantities in a single matrix, the above formulation may be computationally efficient for a radiotherapy treatment planning optimizer. For example, the matrix $A^{GIGRT}$ may be calculated once at the beginning of the optimization process and is not re-calculated at every iteration of the firing filter values. A radiotherapy treatment planning system may be configured to iterate on firing filter values until one or more stopping conditions are met. Such stopping conditions may comprise one or more of the following: dose goals and objectives have been met within an acceptable tolerance, radiation fluence map values have converged such that changes between iterations are less than a predetermined residual criterion, cost function(s) value(s) have converged over multiple iterations, a threshold number of iterations (e.g., an upper limit on the number of total iterations) has been reached, etc. The final firing filter values may be saved in a memory of a radiotherapy treatment planning system. In some variations where the patient platform is stopped at predetermined, discrete platform positions (i.e., beam stations) during the delivery of radiation from the multiple firing positions, the firing filters may be calculated for each firing position over each of the beam stations. For example, a patient platform may have 200 beam stations, where each beam station is about 2 mm from the adjacent beam station.

Firing filters calculated using the methods described herein incorporate the noise characteristics and/or variabilities of a target sensor as part of the calculation. For example, where the target sensor is a position sensor, firing filters may be calculated based on the position sensor characterization PDF, which may be a sensor position characterization PDF or a sensor data error characterization PDF. By doing so, the delivery fluence map calculated during a treatment session by convolving the firing filters with sensor images generated using real-time target sensor data may more accurately direct radiation to the actual location of the patient target region. In contrast, typical radiotherapy treatment methods do not incorporate images of target sensor error and/or variability PDFs as a factor during fluence map optimization. That is, typical treatment planning methods do not define radiation fluence in terms of target sensor data nor target sensor noise or variability, and as such, during a treatment session, radiation delivery may not be able to adapt as accurately to real-time noisy target sensor data.

Figure 4A:
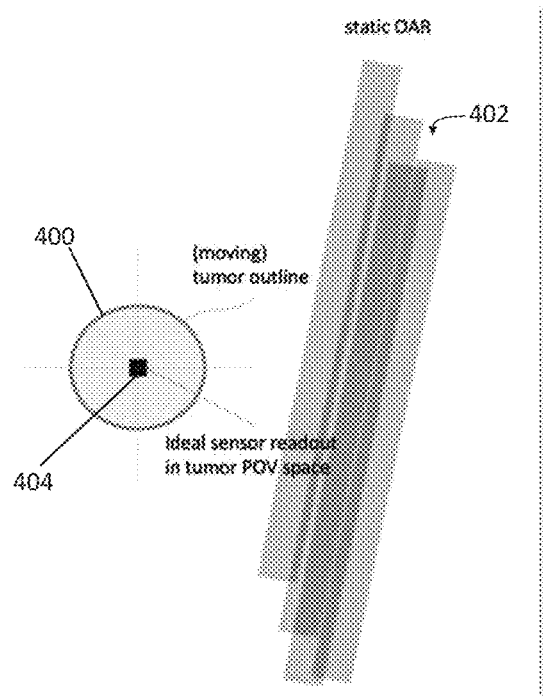
FIGS. 4A-4D depict schematic representations of tumor motion and tumor position in the tumor point-of-view space and the patient point-of-view (static) space based on data from a sensor.
Figure 4B:
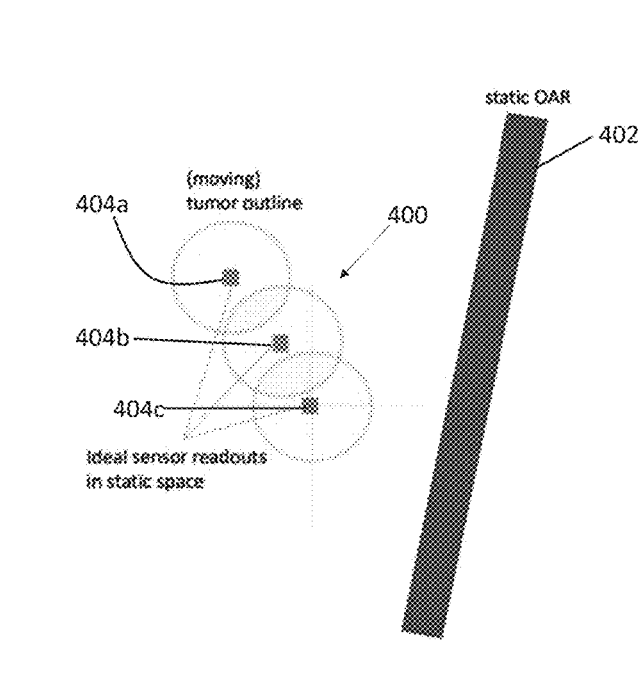

Radiotherapy treatment planning using an image of a target sensor characterization PDF in the methods described above optimize for fluence and calculate firing filters in the tumor point-of-view (POV) frame, as opposed to the static frame. FIGS. 4A-4D depict conceptual diagrams that explain the physical meaning of a target sensor data reading PDF, using a position sensor as an example. One exemplary scenario is a tumor (400) that located near a bone (402), where the tumor (400) is moving, and the bone (402) is static. A position sensor may be coupled to the tumor (e.g., by needle placement using image guidance), for example, in its center, such that the position sensor data reading indicates the location of the tumor centroid. FIG. 4A depicts the tumor (400) and the bone (402) in the tumor POV frame, and the output (404) of an ideal position sensor (i.e., which always gives a true position data value without any variability or errors). In the tumor POV, the origin is at the tumor centroid, and the position sensor outputs a single positional value (404) that reflects the true position of the tumor centroid, e.g., (0,0,0). From the POV of the tumor (400), the bone (402) is moving. FIG. 4B depicts the same tumor (400) and bone (402) in the static frame, and the output (404a-404c) of an ideal position sensor that is coupled to the tumor. In the static frame, the origin is the location of the tumor centroid when the patient is first positioned on the patient platform (e.g., positioned using CT and/or MRI imaging guidance). The ideal position sensor data readings have different values, reflecting the different locations of the moving tumor centroid. This is in contrast to the position sensor data readings in the tumor POV of FIG. 4A, which will always provide the same sensor data reading value. An image of this tumor motion, generated based on the position sensor data readings, may be a tumor position histogram or tumor dwell matrix. Typically, radiotherapy treatment planning systems and methods characterize tumor position in the static frame (FIG. 4B), and not in the tumor POV frame (FIG. 4A), since the position sensor data reading in the static frame reflects the actual position of the tumor in the same reference frame as the radiation therapy system. Furthermore, in the case of an ideal position sensor in the tumor POV frame, the position sensor data reading is constant, despite the motion of tumor.

Figure 4C:
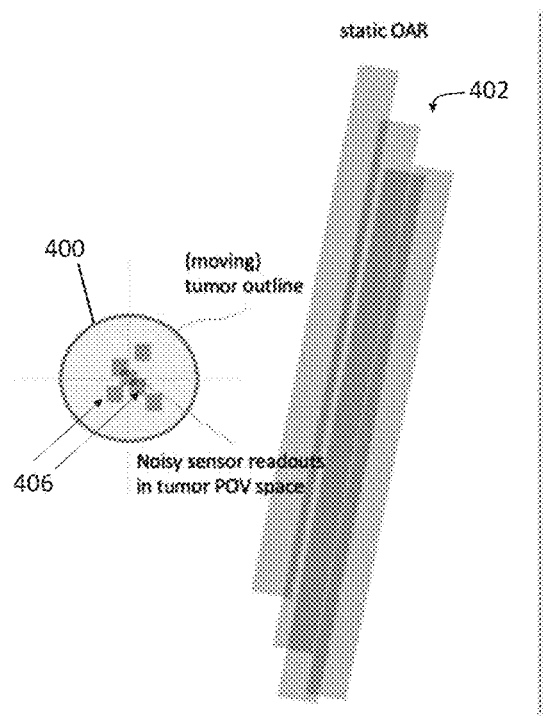
Figure 4D:
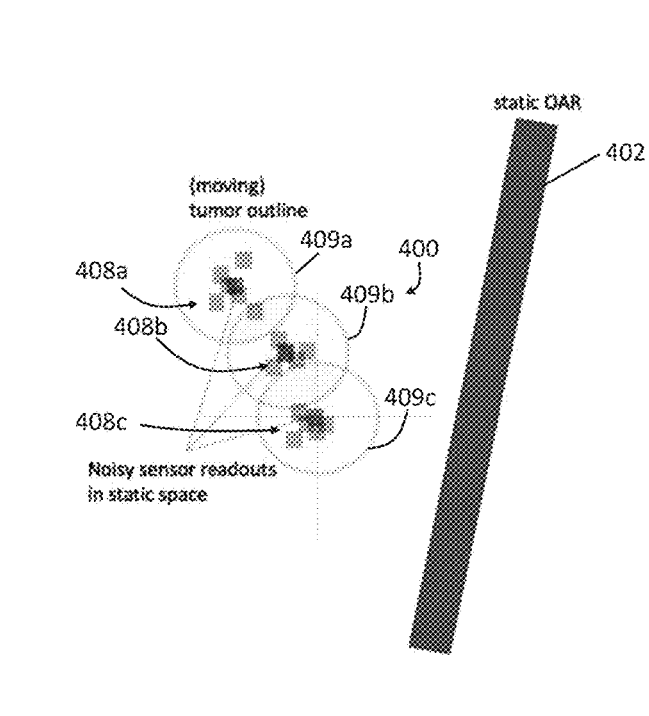

However, in the case of a noisy position sensor, radiotherapy treatment planning in the tumor POV may provide unexpected advantages. These advantages may include, for example, the delivery of radiation that more precisely tracks the patient target region in the presence of a noisy position sensor. Another advantage may include mitigating motion-related dose artifacts that are common when treatment planning is performed in the static frame, which may reduce the irradiation of surrounding non-target tissue while still delivering the prescribed dose to the patient target region. FIG. 4C depicts the tumor (400) and the bone (402) in the tumor POV frame, and the outputs (406) of a noisy position sensor. In contrast with an ideal position sensor, a noisy position sensor may provide different position sensor data readings for the same location in space, where the different readings may be a result of sensor variabilities and/or errors. Such sensor variabilities and/or errors may be represented by a sensor error characterization PDF. In the tumor POV, the origin is at the tumor centroid, and the position sensor outputs multiple positional values (406) in accordance with the sensor error characterization PDF that is centered on the true position data value. As described above, a position sensor error characterization PDF may be known (e.g., measured or derived) prior to a treatment session, notably, regardless of the location or motion of tumor (400). FIG. 4D depicts the same tumor (400) and bone (402) in the static frame, and the outputs (408a-408c) of a noisy position sensor that is coupled to the tumor. In the static frame, the origin may be the location of the tumor centroid when the patient is first positioned on the patient platform (e.g., positioned using CT and/or MRI imaging guidance). For each of the different locations of the moving tumor centroid, the noisy position sensor data readings may be variable. In the example depicted in FIG. 4D, the tumor (400) may move to three locations, and at each of those locations, the position sensor data readings may vary in accordance with the sensor characterization PDF. That is, at a first tumor location (409a), the position sensor data readings may be any of the values in a first cluster (408a) centered around the true position data value of the first location; at a second tumor location (409b), the position sensor data readings may be any of the values in a second cluster (408b) centered around the true position data value of the second location; and at a third tumor location (409c), the position sensor data readings may be any of the values in a third cluster (408c) centered around the true position data value of the third location. The cumulative image of all of the position sensor data readings may depict a blurred tumor image, due to the tumor being "smeared" over its motion trajectory, as well as the variabilities and/or errors in the noisy position sensor. In addition, since the tumor is moving and its location is being tracked with a noisy position sensor (i.e., the true position of the tumor is not known), the position sensor error characterization PDF in the static frame may be difficult to determine.

Radiotherapy treatment planning systems that calculate delivery fluence maps and/or firing filters in the static frame (i.e., using a blurred or "smeared" image of a tumor acquired during treatment planning) may result in delivered doses that are susceptible to motion artifacts (e.g., dose-peaking artifacts). Such motion artifacts may be especially pronounced if the tumor motion on the day of treatment is different from the tumor motion when the treatment planning image was acquired. In contrast, radiotherapy treatment planning methods (such as method (200) and the other methods described herein) that calculate delivery fluence maps and/or firing filters based on a sensor characterization PDF in the tumor POV frame where the tumor is stationary do not require prior knowledge of the tumor motion. Delivery fluence maps and/or firing filters calculated in the tumor POV frame may result in delivered doses that have fewer motion artifacts.

While method (200) was described above in the context of a target sensor that is a position sensor, method (200) is also applicable for target sensor systems that comprise an imaging system. An imaging system may comprise one or more image sensors, including, but not limited to PET detectors, MRI detectors, CT detectors, optical cameras (including cameras for fluoroscopy), and the like. A target sensor characterization PDF for a target sensor system that comprises an imaging system may be a "full" image that has sufficient imaging data to identify the location and/or geometry of a tumor centroid, and/or contour tumor boundaries and/or OAR boundaries. This "full" image L may be obtained during one or more diagnostic imaging sessions by acquiring a plurality of imaging data h and combining (e.g., summing) them to form the treatment planning image. That is, $$L = \Sigma l_j$$

Imaging data $l_j$ may include samples or image sensor readings such as 3-D PET imaging data (e.g., positron annihilation emission paths, which may be referred to as lines-of-response or LORs), 2-D X-ray imaging data, projection imaging data (e.g., X-ray projections), fluoroscopy imaging data, CT imaging data, and/or MR imaging data (sub-samples in k-space from a MRI imaging pulse sequence). In some variations, the treatment planning image may be acquired using an imaging system of a radiation therapy system. For example, the image(s) used for treatment planning may be acquired using the on-board kV CT imaging system and/or MR imaging system and/or PET imaging system of a radiation therapy system. Examples of treatment planning image(s) may include, but are not limited to, 3-D PET images, 2-D X-ray images, X-ray projection images, fluoroscopy images, CT images, and/or MR images. Generating (204) sensor images $N_i$ for each of i firing positions of the therapeutic radiation source may comprise calculating the projection of the "full" image N onto each of the i firing positions. Calculating (206) the shift-invariant firing filters may be performed as described above.

Radiotherapy Delivery Method: Single Sensor

Figure 5:
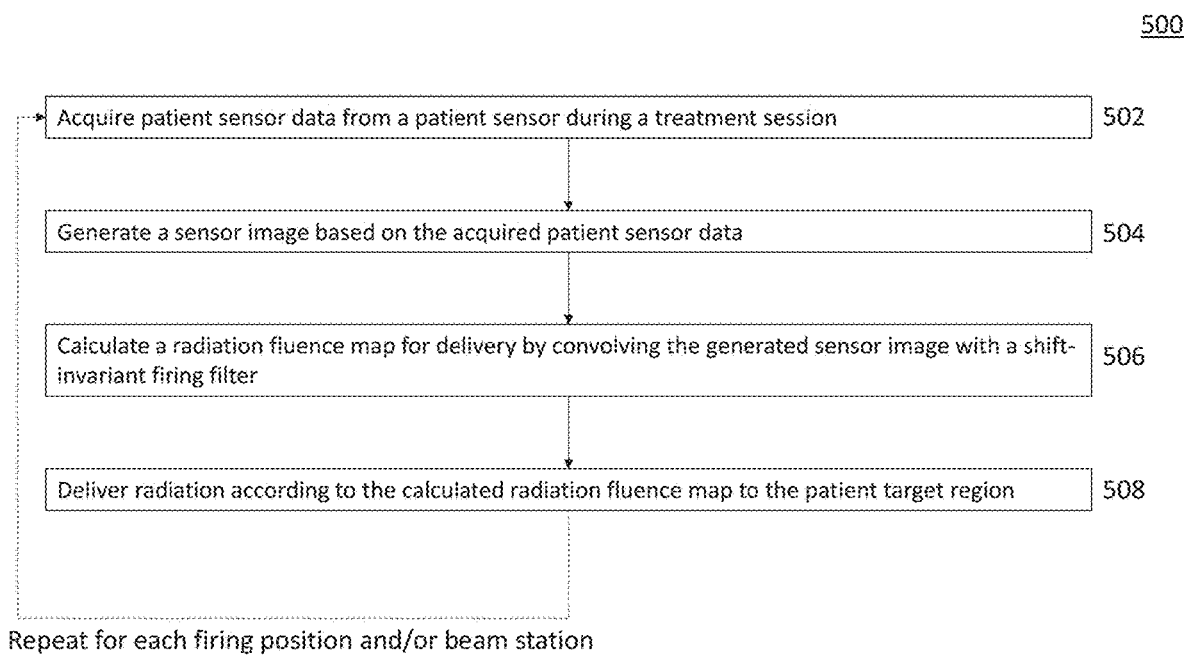
FIG. 5 depicts a flowchart representation of one variation of a radiation delivery method.

FIG. 5 depicts one variation of a radiotherapy delivery method that uses the shift-invariant firing filters calculated during treatment planning (e.g., in accordance with method (200)) and target sensor data acquired during a treatment session from a target sensor (or target sensor system) to calculate the radiation fluence for delivery during that treatment session. Method (500) may comprise acquiring (502) target sensor data during a treatment session (or any radiation-delivery session), generating (504) a sensor image based on the acquired target sensor data, calculating (506) a radiation fluence map for delivery by convolving the generated sensor image with a shift-invariant firing filter, and delivering (508) radiation according to the calculated radiation fluence map to a patient target region. Acquiring (502) target sensor data may comprise acquiring position sensor data readings at the start of the treatment session and/or throughout the treatment session while the therapeutic radiation source is delivering radiation to the patient. Acquiring (502) target sensor data during a treatment session may include acquiring target sensor data solely at the beginning of a treatment session (i.e., before the therapeutic radiation source is activated for the first time) or may include acquiring target sensor data throughout the treatment session. For example, acquiring (502) target sensor data may comprise acquiring a localization CT image and/or a PET prescan image (and/or any of the other previously-described imaging modalities) at the start of the treatment session, and may also include acquiring CT imaging data and/or PET imaging data during the portion of the treatment session when the therapeutic radiation source is delivering radiation to the patient. In some variations, imaging data acquired during the radiation delivery portion of the treatment session may be acquired in short or limited time intervals (e.g., about 30 seconds or less, about 10 seconds or less, about 2 seconds or less, about 1 second or less, about 0.5 second or less, etc.). Target sensor data may be acquired just prior to the delivery of the therapeutic radiation beams. For example, target sensor data may be acquired less than about 5 seconds (e.g., less than about 3 seconds, less than about 2 seconds, less than about 1 second, less than 0.5 second, less than 0.1 second, etc.) prior to radiation delivery. In some variations, target sensor data may be acquired for a firing position (e.g., firing position i) while the therapeutic radiation source is located at a previous firing position (e.g., firing position i–1) and/or while the therapeutic radiation source is moving to the firing position (e.g., in-transit between firing positions). Alternatively, or additionally, target sensor data may be acquired for a firing position (e.g., firing position i) when the therapeutic radiation source is located at that firing position. For example, the imaging data acquired during the radiation delivery portion may be PET LORs, X-ray projections, and/or sub-samples in k-space from an MRI imaging pulse sequence.

Generating (504) a sensor image based on the acquired sensor data may comprise, for example, aggregating the acquired imaging data to generate a map of pixel and/or voxel intensity values. Because the imaging data may be acquired over a limited time interval, the resultant sensor images (or image maps) may be referred to as partial or limited-time sampled (LTS) images. LTS images may have high levels of noise (i.e., high signal-to-noise ratio) such that when considered on their own, may not provide enough information to identify the contours and/or centroid of a patient target region or OAR. Alternatively, or additionally, imaging data may be acquired at the beginning of a treatment session (e.g., CT localization scan and/or PET prescan). In some variations, generating (504) a sensor image may comprise plotting the acquired sensor data reading as a delta function or a Gaussian function that is centered around the sensor data reading. For example, generating (504) a sensor image for that position sensor may comprise plotting the acquired position sensor data reading as a delta function or a Gaussian function that is centered around the position sensor data reading.

Calculating (506) a radiation fluence map for delivery at firing position i may comprise convolving the position sensor image (e.g., a delta function) with a corresponding firing filter p generated during treatment planning using the sensor characterization PDF for that position sensor. For example, to calculate the radiation fluence $f_{i,j}$ for delivery at firing position i, at time instance j, the controller of the radiation therapy system convolves the firing filter corresponding to firing position i with a projection of the position sensor delta function image $\delta_{i,j}$ onto the firing position i:

$$f_{i,j} = p_i * \delta_{i,j}$$

Similarly, in a variation where the target sensor comprises an imaging system, calculating (506) a radiation fluence map for delivery may comprise convolving the partial or LTS image with a corresponding firing filter p generated during treatment planning using a "full" image generated using that imaging system (or the same imaging modality). For example, to calculate the radiation fluence $f_{i,j}$ for delivery at firing position i, at time instance j, the controller of the radiation therapy system convolves the firing filter corresponding to firing position i with a projection of the partial or LTS image $x_{i,j}$ onto the firing position i:

$$f_{i,j} = p_i * x_{i,j}$$

The delivery fluence $f_{i,j}$ is calculated in the static frame, i.e., the same reference frame as the radiation therapy system. During treatment planning, the firing filters p were calculated and optimized in the tumor POV frame. However, because the firing filters p are shift-invariant, they may be applied to target sensor data acquired in the static frame, and may still result in the delivery of therapeutic radiation that meets the prescribed dose (e.g., dose goals and objectives).

In variations where the patient platform is stopped at a series of predetermined, discrete platform positions (i.e., beam stations) during radiation delivery, method (500) may be repeated for each beam station. For example, a radiotherapy delivery method may comprise moving the patient platform to a first beam station, calculating a radiation fluence map for delivery based on target sensor data readings using the methods described herein (e.g., method (500)), delivering radiation to the patient target region by emitting radiation from the therapeutic radiation from the i firing positions, then moving the patient platform to a second beam station, and repeating the calculation and delivery of radiation fluence as described herein. This may be repeated for all of the beam stations that were defined during radiotherapy treatment planning. For example, a patient platform may have 200 beam stations, where each beam station is about 2 mm from the adjacent beam station. The radiotherapy treatment planning system may be configured to calculate i firing filters (one for each of i firing positions over all beam stations), and transfer these i firing filters to the radiation therapy system controller memory. During the treatment session, the radiation therapy system controller may move the patient platform to the first beam station b1, retrieve the firing filters from the controller memory, and calculate the radiation fluence map $f_{i,b1}$ for delivery at firing position i by convolving the projection of the target sensor image ($x_{i,b1}$) on firing position i at the first beam station b1 with the firing filter $p_i$, and so forth for all firing positions at the first beam station. In some variations (e.g., where the radiotherapy system comprises a 1-D MLC), calculating the radiation fluence map $f_{i,b1}$ for delivery may further comprise extracting the slice of the fluence (i.e., the convolution of the projection of the target sensor image ($x_{i,b1}$) on firing position i at the first beam station b1 with the firing filter $p_i$) that corresponds with the MLC field-of-view at firing position i. The radiation fluence map $f_{i,b1}$ for delivery may then be segmented into MLC openings, and then the fluence map may be delivered by the therapeutic radiation source (e.g., linac pulses). After the therapeutic radiation source delivers the radiation fluence map $f_{i,b1}$ for all of the firing positions i at the first beam station b1, the radiation therapy system controller may then move the patient platform to the second beam station b2 and perform similar calculations and radiation delivery, and repeat this for each of the firing positions at the 200 beam stations.

Method (500) may also be used in a non-therapeutic manner, for example, in a QA session where the patient is replaced with a phantom and/or fluence measurement device. Optionally, the phantom and/or fluence measurement device may be mounted on a motion stage, which may be a mechanical apparatus configured to move the phantom and/or fluence measurement device according to motion trajectories that simulate patient and/or patient target region motion. The motion may be based, in some variations, on a motion dwell histogram for the target region. The phantom(s) and/or fluence measurement device(s) may be set up with target sensors and/or target sensor system as described above with a patient. As applied to a non-therapeutic radiation delivery session (e.g., a QA session), method (500) may comprise acquiring (502) target sensor data during the QA session, generating (504) a sensor image based on the acquired target sensor data, calculating (506) a radiation fluence map for delivery by convolving the generated sensor image with a shift-invariant firing filter, and delivering (508) radiation according to the calculated radiation fluence map to a target region (e.g., a phantom target region).

Radiotherapy Treatment Planning Method: Two or More Sensors

Figure 6:
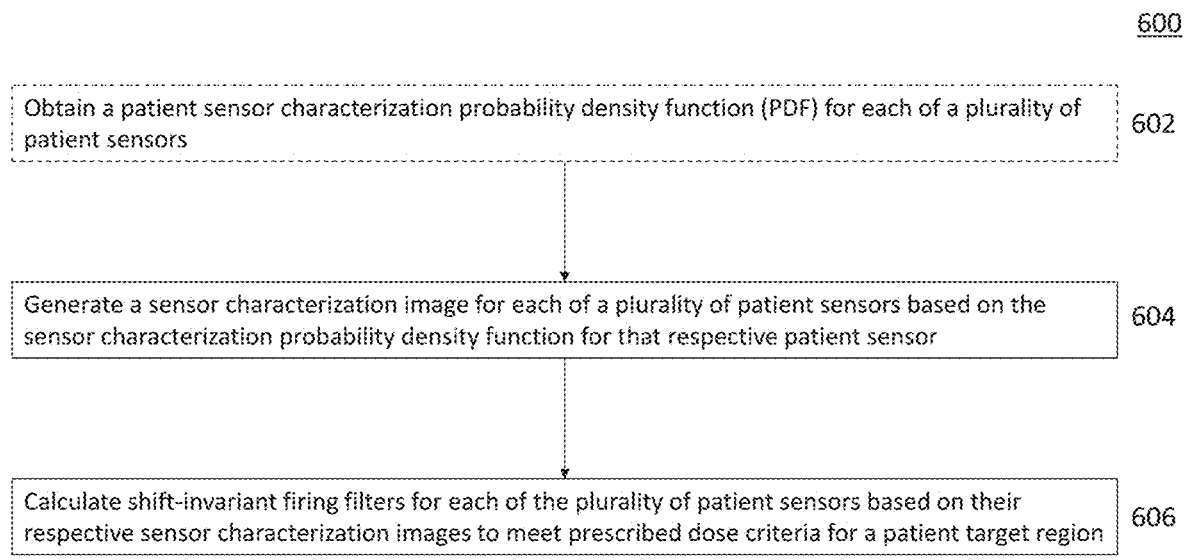
FIG. 6 depicts a flowchart representation of a treatment planning method that incorporates target sensor data from multiple target sensors.

One variation of a radiotherapy treatment planning method that incorporates target sensor data from multiple target sensors (i.e., two or more target sensors) is depicted in FIG. 6. Method (600) may comprise obtaining (602) the target sensor characterization PDF for each of a plurality of target sensors, generating (604) target sensor characterization images for each of the target sensors that are based on that sensor's characterization PDF, and calculating (606) shift-invariant firing filters for each of the target sensors based on their respective sensor characterization images to meet prescribed dose criteria for a patient target region. The number and type of target sensors in radiotherapy treatment planning may correspond to the number and type of target sensors that will be used during the treatment session. The target sensors may all be one sensing modality or a mix of different sensing modalities. For example, the plurality of target sensors may comprise imaging systems of different imaging modalities (e.g., a CT imaging system and a PET imaging system, a PET imaging system and a fluoroscopy system, a PET imaging system and an optical camera, a MR imaging system and an optical camera, etc.), or multiple imaging systems of the same imaging modality (e.g., a first CT imaging system and a second CT imaging system). The plurality of target sensors may comprise a plurality of position sensors, some of which may be coupled to the patient at anatomical structures whose location and/or motion may be correlated with the location and/or motion of a patient target region and/or OAR. The plurality of target sensors may comprise one or more imaging systems and one or more position sensors.

In some variations, the target sensor characterization PDF for the plurality of target sensors may be provided by previous models and/or calculations, in which case, obtaining (602) the sensor characterization PDF of the target sensors may be optional. As described previously, the sensor characterization PDF for each of the plurality of target sensors may be derived from a plurality of target sensor data. The image of the sensor characterization PDF may be the sum of the images of the plurality of target sensor characterization data. In the example where there are two target sensors, the image of the sensor characterization PDF for each of the target sensors may be given by:

$X = \Sigma x_j$ $Y = \Sigma y_j$ where x and y are images of individual sensor data readings, and X and Y are the sensor characterization PDF for the first and second target sensors, respectively. For example, $x_j$ may be images of j position sensor data readings (e.g., a delta function or Gaussian function centered around the position sensor data reading) and X is an image of the position sensor characterization PDF. The second system may be, for example, a PET imaging system, and $y_j$ may be j samples of PET imaging data (e.g., j LORs) and Y is a PET image that is used for treatment planning.

Generating (604) a sensor characterization image may comprise generating a first image X of the first target sensor for each of i firing positions and generating a second image Y of the second target sensor for each of i firing positions. For example, to generate a radiotherapy treatment plan for a radiation therapy system that has 50 firing positions, generating (604) a sensor characterization image for each of the target sensors may comprise generating a series of sensor characterization images $X_i$ that are a projection of image X on each of the i firing positions for the first target sensor, and generating a series of sensor characterization images $Y_i$ that are a projection of image Y on each of the i firing positions for the second target sensor.

Calculating (606) shift-invariant firing filters for each of the target sensors may comprise calculating a firing filter for each of the target sensors for each firing position. That is, each target sensor has its own set of i firing filters. For example, a radiotherapy treatment planning system may be configured to calculate a first set of shift-invariant firing filters $p_i$ for the first target sensor (over i firing positions) and to calculate a second set of shift-invariant firing filters $q_i$ for the second target sensor. Expanding upon the firing filter calculation methods described above, the radiation fluence map $F_i$ for delivery at firing position i to a patient target region may be represented as:

$F_i = p_i * X_i + q_i * Y_i$

The radiation fluence map $F_i$ for delivery may be the sum of the firing filter and target sensor data convolutions assuming that both of the target sensors shift in concert with the patient target region. The above formulation, along with the optimization methods described below, may be expanded to include an arbitrarily large number of target sensors.

The radiation fluence F (e.g., fluence map) over multiple firing positions (e.g., i number of firing positions) may be represented by:

$$F = \begin{bmatrix} p_0 * X_0 + q_0 * Y_0 \\ \vdots \\ p_{i-1} * X_{i-1} + q_{i-1} * Y_{i-1} \end{bmatrix}$$

For example, the radiation fluence for 50 firing positions may be:

$$F = \begin{bmatrix} p_0 * X_0 + q_0 * Y_0 \\ \vdots \\ p_{49} * X_{49} + q_{49} * Y_{49} \end{bmatrix}$$

Expanding on the dose formulation described above, where A is a dose calculation matrix, and D is the dose cumulative over i firing positions (which may be specified by a clinician when they define the dose prescription and/or goals):

$$D = A \cdot F$$

$$D = A \cdot \begin{bmatrix} p_0 * X_0 + q_0 * Y_0 \\ \vdots \\ p_{i-1} * X_{i-1} + q_{i-1} * Y_{i-1} \end{bmatrix}$$

where $p_0 \ldots p_{i-1}$ are the firing filters for the first target sensor, and $q_0 \ldots q_{i-1}$ are the firing filters for the second target sensor over i firing positions.

Dose D may be constrained by one or more cost or penalty functions C(D,F), as described previously. To calculate (606) firing filters (e.g., shift-invariant firing filters) in accordance with method (600), a radiotherapy treatment planning system may set up an optimization problem for minimizing the cost function C(D, F), given a dose calculation matrix A and target sensor characterization images X and Y. Calculating firing filters p and q may comprise iterating through different firing filter values such that the cost function C(D, F) is minimized while still attaining dose goals and objectives in accordance with the dose prescription:

$$D = A \cdot \begin{bmatrix} p_0 * X_0 + q_0 * Y_0 \\ \vdots \\ p_{i-1} * X_{i-1} + q_{i-1} * Y_{i-1} \end{bmatrix}$$

$$D = A \cdot \begin{bmatrix} toep(X_0) & & toep(Y_0) & \\ & \ddots & & \ddots \\ & & toep(X_{i-1}) & & toep(Y_{i-1}) \end{bmatrix} \cdot \begin{bmatrix} p_0 \\ \vdots \\ p_{i-1} \\ q_0 \\ \vdots \\ q_{i-1} \end{bmatrix}$$

where the convolution of target sensor characterization images X and Y with firing filters p and q has been converted to a matrix multiplication between a block diagonal of Toeplitz matrices of the target sensor characterization images and a column vector of firing filters for each firing position (in this case, two sets of firing filters). Since the dose calculation matrix A and the target sensor characterization images X and Y are known (i.e., previously calculated based on treatment planning images, target sensor data, target sensor PDF, etc.), they may be combined into a single matrix, denoted $A^{GIGRT}$.

$$D = A^{GIGRT} \cdot \begin{bmatrix} p_0 \\ \vdots \\ p_{i-1} \\ q_0 \\ \vdots \\ q_{i-1} \end{bmatrix}$$

By grouping the known quantities in a single matrix, the above formulation may be computationally efficient for a radiotherapy treatment planning optimizer. For example, the matrix $A^{GIGRT}$ may be calculated once at the beginning of the optimization process and is not re-calculated at every iteration of the firing filter values. A radiotherapy treatment planning system may be configured to iterate on firing filter values p and q until one or more stopping conditions (such as any of the previously-described stopping conditions) are met. The final firing filter values p and q may be saved in a memory of a radiotherapy treatment planning system. In some variations where the patient platform is stopped at predetermined, discrete platform positions (i.e., beam stations) during the delivery of radiation from the multiple firing positions, and the radiotherapy treatment planning system may calculate firing filters over all beam stations. For example, a patient platform may have 200 beam stations, where each beam station is about 2 mm from the adjacent beam station. During radiotherapy treatment planning, method (600) may be used to calculate two sets of i firing filters (p and q, each set having i firing filters, one for each of i firing position) that may be applied over the 200 beam stations.

Radiotherapy Delivery Method: Two or More Sensors

Figure 7:
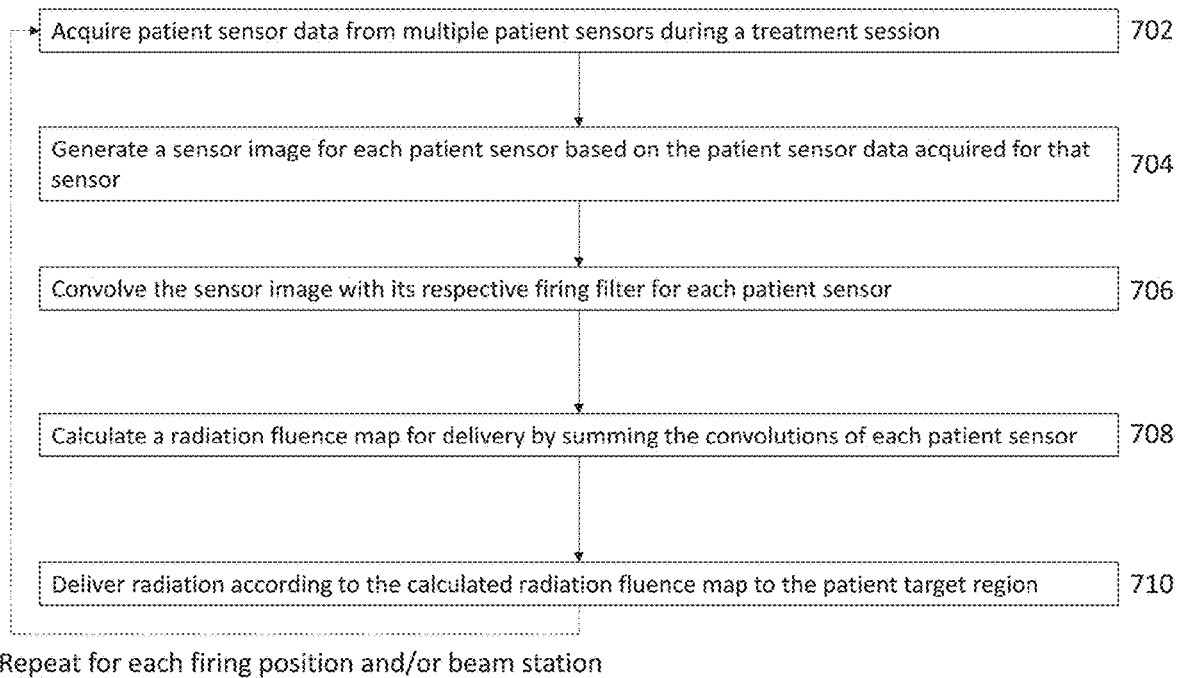
FIG. 7 depicts a flowchart representation of one variation of a radiation delivery method.

FIG. 7 depicts one variation of a radiotherapy delivery method that uses the multiple sets of shift-invariant firing filters calculated during treatment planning (e.g., in accordance with method (600)) and target sensor data acquired during a treatment session from multiple target sensors (or target sensor systems) to calculate the radiation fluence for delivery during that treatment session. Method (700) may comprise acquiring (702) target sensor data from multiple target sensors during a treatment session (or any radiation-delivery session), generating (704) a sensor image for each target sensor based on the target sensor data acquired for that sensor, convolving (706) the generated sensor image with its respective firing filter for each target sensor, calculating (708) a radiation fluence map for delivery by summing the convolutions of each target sensor, and delivering (710) radiation according to the calculated radiation fluence map to the patient target region. Target sensor data may be acquired from any combination of target sensors as described previously; the number and/or type of target sensors and/or target sensor systems may be determined by a clinician. For example, target sensor data may be acquired from a PET imaging system and one or more position sensors. Target sensor data may be acquired from an X-ray imaging system (e.g., CT imaging system) or a MR imaging system, and one or more position sensors. Acquiring (702) target sensor data may comprise acquiring position sensor data readings from the multiple target sensors at the start of the treatment session and/or throughout the treatment session while the therapeutic radiation source is delivering radiation to the patient. Acquiring (702) target sensor data during a treatment session may include acquiring target sensor data from one or more of the multiple target sensors solely at the beginning of a treatment session (i.e., before the therapeutic radiation source is activated for the first time), or may include acquiring target sensor data from one or more of the multiple target sensors throughout the treatment session. For example, acquiring (702) target sensor data may comprise acquiring a localization CT image and/or a PET prescan image (and/or any of the other previously-described imaging modalities) at the start of the treatment session, and may also include acquiring CT imaging data and/or PET imaging data during the portion of the treatment session when the therapeutic radiation source is delivering radiation to the patient. Acquiring (702) target sensor data may comprise acquiring a patient localization CT image and/or a PET prescan at the start of the treatment session, and acquiring position sensor data during the radiation delivery portion of the treatment session. In some variations, imaging data acquired during the radiation delivery portion of the treatment session may be acquired in short or limited time intervals (e.g., about 2 seconds or less, about 1 second or less, about 0.5 second or less, etc.). For example, the imaging data acquired during the radiation delivery portion may be PET LORs, X-ray projections, and/or sub-samples in k-space from an MRI imaging pulse sequence. Target sensor data may be acquired just prior to the delivery of the therapeutic radiation beams. For example, target sensor data may be acquired less than about 5 seconds (e.g., less than about 3 seconds, less than about 2 seconds, less than about 1 second, etc.) prior to radiation delivery. In some variations, target sensor data may be acquired for a firing position (e.g., firing position i) while the therapeutic radiation source is located at a previous firing position (e.g., firing position i−1) and/or while the therapeutic radiation source is moving to the firing position (e.g., in-transit between firing positions). Alternatively, or additionally, target sensor data may be acquired for a firing position (e.g., firing position i) when the therapeutic radiation source is located at that firing position.

In some variations, generating (704) a sensor image may comprise plotting the acquired sensor data reading as a delta function or a Gaussian function that is centered around the sensor data reading. For example, generating (704) a sensor image $x_i$ for that position sensor may comprise plotting the acquired position sensor data reading as a delta function or a Gaussian function that is centered around the position sensor data reading. Alternatively, or additionally, generating (704) a sensor image $y_i$ for an imaging system may comprise, for example, aggregating the acquired imaging data to generate a map of pixel and/or voxel intensity values. Because the imaging data may be acquired over a limited time interval, the resultant sensor images (or image maps) may be referred to as partial or limited-time sampled (LTS) images. LTS images may have high levels of noise (i.e., high signal-to-noise ratio) such that when considered on their own, may not provide enough information to identify the contours and/or centroid of a patient target region or OAR. Alternatively, or additionally, imaging data may be acquired at the beginning of a treatment session (e.g., CT localization scan and/or PET prescan). While the examples here are in the context of treating a patient based on target sensor data from a position sensor (first target sensor) and an imaging system (second target sensor system), it should be understood that similar methods may be applied to any number and/or types of target sensors and combinations thereof, as previously described.

Convolving (706) the sensor image with its respective firing filter may comprise retrieving, from a memory of the radiation therapy system controller, the firing filter calculated during treatment planning for that particular target sensor and firing position i, calculating a projection of the sensor image onto firing position i, at time instance j, and convolving the firing filter and the projected image. These steps may be repeated for each of the target sensors. That is, for the first target sensor:

$$p_i * x_{i,j}$$

where $p_i$ is the firing filter for firing position i for the first target sensor, $x_{i,j}$ is the projection of the first target sensor data at time instance j onto firing position i. For example, in the variation where the first target sensor is a position sensor, the sensor image may be a position sensor delta function $\delta_j$, and $\delta_{i,j}$ may be the projection of the delta function image onto the firing position i.

$$p_i * \delta_{i,j}$$

For the second target sensor:

$$q_i * y_{i,j}$$

where $q_i$ is the firing filter for firing position i for the second target sensor, $y_{i,j}$ is the projection of the second target sensor data at time instance j onto firing position i. For example, in the variation where the second target sensor system is an imaging system, the sensor image may be a LTS image, and the radiation therapy system controller may be configured to convolve the firing filter with the projection of the LTS image onto the firing position i. The convolution of firing filters with projections of images of sensor data onto a firing position may be calculated for any number of (e.g., all of) the target sensors that are used during a treatment session and for which corresponding firing filters were calculated during treatment planning.

Calculating (706) a radiation fluence map $f_{i,j}$ for delivery at firing position i based on target sensor data acquired at time instance j may comprise summing the convolutions (704):

$$f_{i,j} = p_i * x_{i,j} + q_i * y_{i,j}$$

In the example where the first target sensor is a position sensor, and the position sensor image is a delta function:

$$f_{i,j} = p_i * \delta_{i,j} + q_i * y_{i,j}$$

As with the delivery fluence calculation for a single target sensor, the delivery fluence $f_{i,j}$ is calculated in the static frame, i.e., the same reference frame as the radiation therapy system. During treatment planning, the firing filters p and q were calculated and optimized in the tumor POV frame. However, because the firing filters p are shift-invariant, they may be applied to target sensor data acquired in the static frame, and may still result in the delivery of therapeutic radiation that meets the prescribed dose (e.g., dose goals and objectives) in the tumor POV frame.

In variations where the patient platform is stopped at a series of predetermined, discrete platform positions (i.e., beam stations) during radiation delivery, method (700) may be repeated for each beam station. For example, a radiotherapy delivery method may comprise moving the patient platform to a first beam station, calculating a radiation fluence map for delivery based on target sensor data readings using the methods described herein (e.g., methods (500), (700)), delivering radiation to the patient target region by emitting radiation from the therapeutic radiation from the i firing positions, then moving the patient platform to a second beam station, and repeating the calculation and delivery of radiation fluence as described herein. This may be repeated for all of the beam stations that were defined during radiotherapy treatment planning. For example, a patient platform may have 200 beam stations, where each beam station is about 2 mm from the adjacent beam station. In this example, the therapeutic radiation source may be configured to emit radiation at 100 firing positions (i=100). If two target sensors (and/or target sensor systems) are used, then the radiotherapy treatment planning system may be configured to calculate 2 sets of firing filters (each set having 100 firing filters one for each of i=100 firing positions), one set of 100 firing filters for the first target sensor and a second set of 100 firing filters for the second target sensor. The planning system may transfer these two sets of firing filters to the radiation therapy system controller memory. During the treatment session, the radiation therapy system controller may move the patient platform to the first beam station, retrieve the firing filters from the controller memory, and calculate the radiation fluence map for delivery at firing position i by summing the convolution of the first target sensor image with its corresponding firing filter, and the convolution of the second target sensor image with its corresponding firing filter. In some variations (e.g., where the radiotherapy system comprises a 1-D MLC), calculating the radiation fluence map for delivery may further comprise extracting a slice of the fluence generated by the convolution of the first target sensor image with its corresponding firing filter that corresponds with the MLC field-of-view at a firing position, and extracting a slice of the fluence generated by the convolution of the second target sensor image with its corresponding firing filter, that corresponds with the MLC field-of-view at the (same) firing position, and then summing the fluence slices to obtain the radiation fluence map for delivery. After the therapeutic radiation source delivers the radiation fluence map for all of the i firing positions at the first beam station, the radiation therapy system controller may then move the patient platform to the second beam station and perform similar calculations and radiation delivery, and repeat this for each of the firing positions at the 200 beam stations.

Method (700) may also be used in a non-therapeutic manner, for example, in a QA session where the patient is replaced with a phantom and/or fluence measurement device. Optionally, the phantom and/or fluence measurement device may be mounted on a motion stage, which may be a mechanical apparatus configured to move the phantom and/or fluence measurement device according to motion trajectories that simulate patient and/or patient target region motion. The motion may be based, in some variations, on a motion dwell histogram for the target region. The phantom(s) and/or fluence measurement device(s) may be set up with target sensors and/or target sensor system as described above with a patient. As applied to a non-therapeutic radiation delivery session (e.g., a QA session), method (700) may comprise acquiring (702) target sensor data from multiple target sensors during the QA session, generating (704) a sensor image for each target sensor based on the target sensor data acquired for that sensor, convolving (706) the sensor image with its respective firing filter for each target sensor, calculating (708) a radiation fluence map for delivery by summing the convolutions of each target sensor, and delivering (710) radiation according to the calculated radiation fluence map to a target region (e.g., a phantom target region).

Radiotherapy Treatment Planning Method: Constant-Value Sensor

Another variation of a radiotherapy treatment planning method may incorporate data from a target sensor where the sensor data reading is a constant value in the static frame (which is also the same frame of reference as the radiation therapy system and the patient). Because the sensor data reading is a constant value, such a sensor may be called a "null sensor" or a constant-value sensor. A constant-value sensor may be a sensor where the sensor reading does not change; that is, the sensor data reading returns the same value or readout. In some variations, a constant-value sensor may be a target sensor whose sensor output is read-out only once during a radiation delivery session, for example, only once during a treatment session (or only once per patient localization, which may occur more than once during a treatment session, in some variations). One example of a constant-value sensor may be a position sensor where the radiation therapy system reads out the position sensor data reading once during a radiotherapy session. In some variations, constant-value sensor system(s) may comprise CT imaging system and/or PET imaging system that acquires imaging data during the patient localization phase at the beginning of a treatment session, but does not acquire imaging data during the radiation delivery phase of the treatment session. A CT localization image and/or PET prescan image may be used to identify the initial position of a patient target region centroid and/or the initial boundaries of the patient target region. In some variations, the CT localization image and/or PET prescan image may be used to identify a location (in the static frame) of the center of a patient target region motion envelope (e.g., center of a tumor motion envelope or internal target volume or ITV).

Figure 8A:
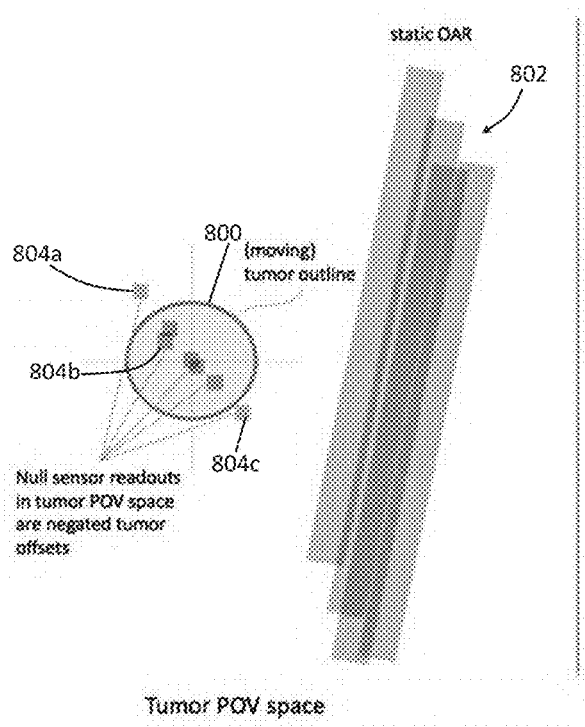
FIGS. 8A-8D depict schematic representations of tumor motion and position in the tumor point-of-view space and the patient point-of-view (static) space based on data from a constant-value ("null") sensor.
Figure 8B:
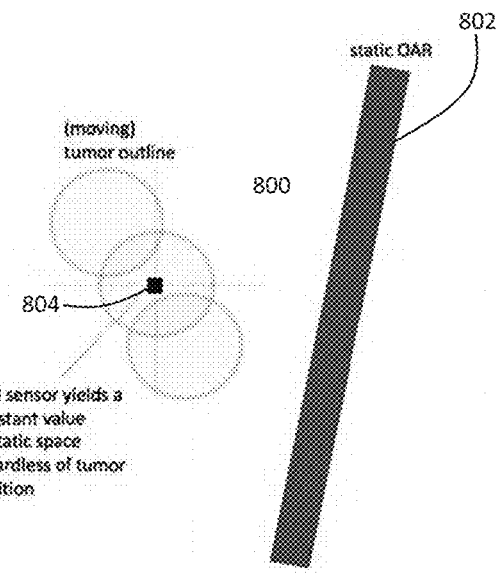
Figure 8C:
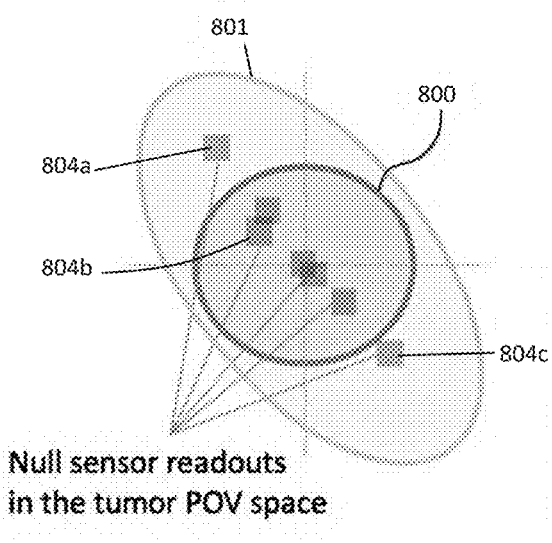
Figure 8D:
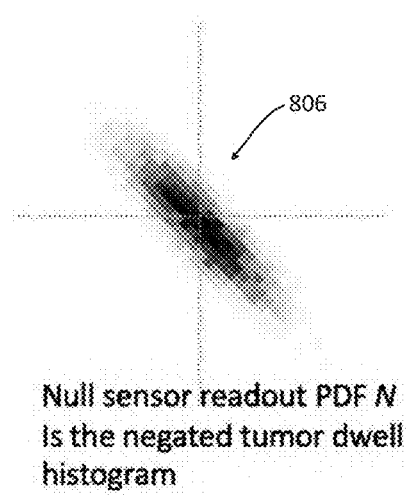

FIGS. 8A-8D depict conceptual diagrams that explain the physical meaning of a constant-value sensor in the tumor POV frame and the static frame, using a constant-value target sensor that outputs the initial location of a tumor centroid in the static frame. The location of the tumor centroid in the stationary frame may be identified using any appropriate sensor modality, including but not limited to one or more of CT imaging, PET imaging, MR imaging, optical imaging using visible or infrared light, position sensing (e.g., using a sensor attached to the tumor and/or nearby landmark, X-ray tracking of a fiducial attached to the tumor and/or nearby landmark, etc.) and the like. In this example, the constant-value target sensor may be a position sensor that outputs the initial portion of the target region (e.g., tumor) centroid in the static frame. Alternatively, or additionally, the constant-value target sensor may be a target sensor system that includes an imaging system, and the location of the tumor centroid may be calculated based on imaging data acquired by the imaging system. FIG. 8A depicts the depicts the tumor (800) and the bone (802) in the tumor POV frame, where the origin (0,0,0) is at the centroid of the tumor (800), while FIG. 8B depicts the tumor (800) and the bone (802) in the static frame, where the origin (0,0,0) is at the initial location of the tumor centroid. FIG. 8C depicts an enlarged view of the tumor (800) and the ITV (801) in the tumor POV frame. Alternatively, or additionally, the origin (0,0,0) of the tumor POV frame may be the centroid of the ITV. The boundaries of the ITV may be defined in the static frame and may encompass a volume within which the tumor moves (e.g., motion envelope). As depicted in FIG. 8B, the constant-value sensor reading (804) is unchanged; it remains the same regardless of the motion (i.e., position changes) of the tumor (800) and represents, in this example, the location of the tumor centroid. However, because the tumor (800) is moving relative to the constant-value sensor reading (804), in the tumor POV frame where the tumor is stationary, it would appear that the sensor reading (804) is changing, i.e., is not constant. FIG. 8A and FIG. 8C conceptually depict the stationary tumor (800) in the tumor POV frame, where the tumor (800) is while the sensor reading (which is reflects a value in the static frame) appears to vary across different values (804a-804c, for example). Although the constant-value sensor gives a constant reading (804) in the static frame, regardless of the actual tumor location, in the tumor POV frame, the values (804a-804c) of the sensor reading may reflect the offset of that constant sensor reading to the actual location of the tumor centroid. Therefore, in the tumor POV frame, the sensor reading may be the inverted (or negated) tumor offset from the tumor centroid and/or ITV center. The tumor offset from the centroid may be derived from a tumor position histogram (e.g., tumor dwell matrix), which may be generated using imaging data from a set of 4D CT images, 4D PET data, 4D MR data, patient surface sensors coupled with motion models, dual projective X-ray systems coupled with motion models, for example. FIG. 8D is a plot of a negated tumor position histogram in the tumor POV frame. The plot in FIG. 8D may be an image of the constant-value sensor characterization PDF (806) in the tumor POV frame. That is, the motion of the tumor (800) in the static frame may be represented in the tumor POV frame as a sensor characterization PDF of the constant-value target sensor. The tumor motion may be re-cast, in the tumor POV frame, as the error, variability, or noise of the constant-value target sensor. Accordingly, a radiotherapy treatment planning system may be configured to calculate firing filters using the sensor characterization PDF (806) in the tumor POV frame. In some variations, the range or span of the of the sensor characterization PDF (806) in the tumor POV frame may be less than the range or span of the ITV (801) that is defined in the static frame. Other treatment planning methods and systems optimize the fluence map and/or firing filters based on the ITV as defined in the static frame, however, the methods described herein optimize the fluence map and/or firing filters based on the sensor characterization PDF in the tumor POV space. Calculating firing filters based on the sensor characterization PDF (806) in the tumor POV frame instead of the ITV (801) in the static frame may help reduce the irradiation of healthy tissues surrounding the tumor (800).

Figure 9:
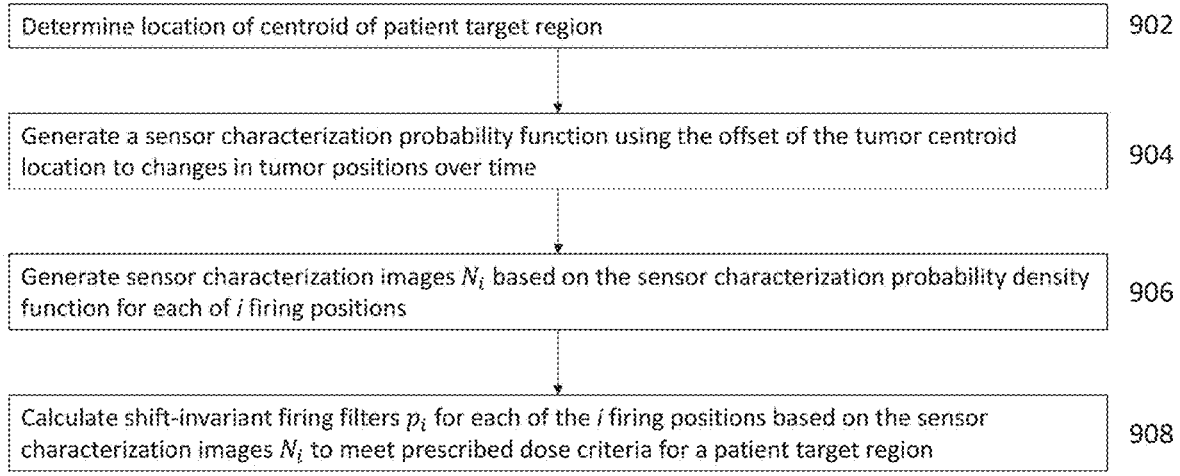
FIG. 9 depicts a flowchart representation of a treatment planning method that incorporates target sensor data from a target sensor.

The sensor characterization PDF of a constant-value target sensor may be used to calculate firing filters according to any of the methods described herein. FIG. 9 depicts one example of a radiotherapy treatment planning method that uses the sensor characterization PDF of a constant-value target sensor to calculate firing filters. The constant-value target sensor may be any sensor or sensor system that outputs the same target region (e.g., tumor) centroid location in the static frame. In some variations, the constant-value target sensor reading may be a position sensor data reading, and in other variations, the constant-value target sensor reading may be a location of the tumor centroid determined based on a treatment planning image. Method (900) may comprise determining (902) a location of a centroid of a tumor (or any patient target region), generating (904) a sensor characterization PDF using the offset of the tumor centroid location relative to changes in the tumor position over time, generating (906) sensor characterization images based on the sensor characterization PDF for each of i firing positions, and calculating (908) shift-invariant firing filters for each of the i firing positions based on the sensor characterization images to meet prescribed dose criteria for the tumor (or patient target region). Determining (902) a centroid of the tumor and generating (904) a sensor characterization PDF may comprise acquiring tumor position data readings over time. In some variations, this may comprise acquiring multiple CT images over time (e.g., 4-D CT imaging), identifying an initial position of the tumor centroid, and then calculating the changes in the centroid location over time. Alternatively, or additionally, acquiring tumor position data readings over time may comprise attaching a position sensor or trackable fiducial to the tumor, identifying an initial position of the tumor centroid, and then measuring the changes in the centroid location over time. Generating (906) sensor characterization images may comprise converting the locational changes may into delta functions or Gaussian functions, as described previously, and aggregating the delta functions or Gaussian functions to obtain an image of the sensor characterization PDF (i.e., sensor characterization PDF image N). In some variations, images of locational changes may include a tumor dwell matrix (e.g., tumor position histogram), which may be negated to obtain an image of the sensor characterization PDF. Generating (906) sensor characterization images may comprise calculating the projection of the sensor characterization PDF N onto each of the i firing positions to obtain sensor characterization images $N_i$. Calculating (908) shift-invariant firing filters ($p_i$) for each of the i firing positions may be similar to the calculation methods described above for methods (200, 600). That is, the dose in the tumor POV may be expressed as follows:

$$D = A \cdot F$$

$$D = A \cdot \begin{bmatrix} p_0 * N_0 \\ \vdots \\ p_{i-1} * N_{i-1} \end{bmatrix}$$

$$D = A \cdot \begin{bmatrix} N_0 * p_0 \\ \vdots \\ N_{i-1} * p_{i-1} \end{bmatrix} = A \cdot \begin{bmatrix} toep(N_0) & & \\ & \ddots & \\ & & toep(N_{i-1}) \end{bmatrix} \cdot \begin{bmatrix} p_0 \\ \vdots \\ p_{i-1} \end{bmatrix}$$

$$D = A^{GIGRT} \cdot \begin{bmatrix} p_0 \\ \vdots \\ p_{i-1} \end{bmatrix}$$

A radiotherapy treatment planning system may be configured to iterate on firing filter values until one or more stopping conditions are met. The final firing filter values may be saved in a memory of a radiotherapy treatment planning system.

Radiotherapy Delivery Method: Constant-Value Sensor

Figure 10:
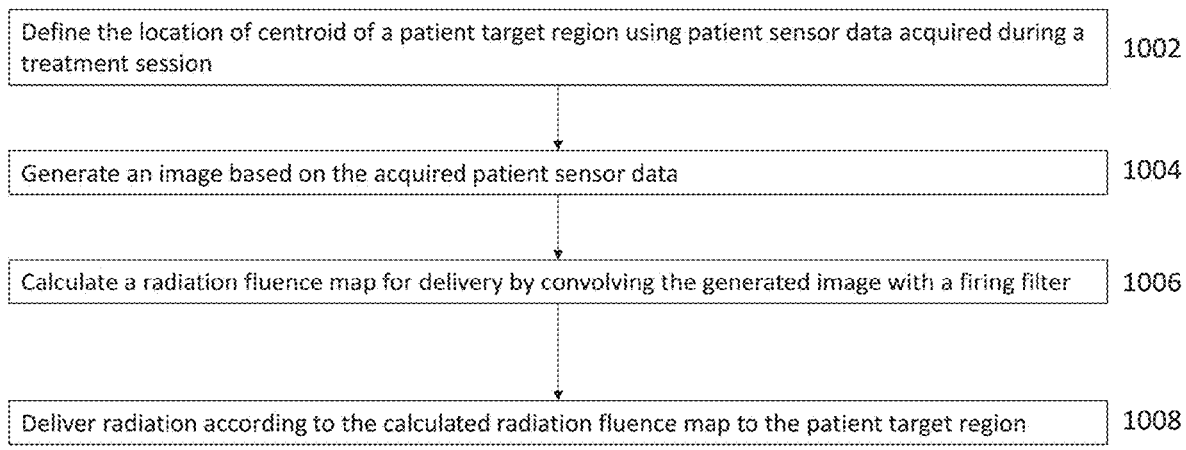
FIG. 10 depicts a flowchart representation of one variation of a radiation delivery method.

FIG. 10 depicts one variation of a radiotherapy delivery method that uses the shift-invariant firing filters calculated during treatment planning (e.g., in accordance with methods (200, 600, 900)) and target sensor data acquired from a constant-value sensor (or sensor system) during a treatment session to calculate the radiation fluence for delivery during that treatment session. Method (1000) may comprise defining (1002) the location of a centroid of a patient target region using target sensor data acquired during a treatment session (or any radiation-delivery session), generating (1004) an image based on the sensor data, calculating (1006) a radiation fluence map for delivery by convolving the generated image with a firing filter, and delivering (1008) radiation according to the calculated radiation fluence map. Defining (1002) the location of the patient target region centroid and generating (1004) a sensor image may comprise acquiring CT and/or PET imaging data to form one or more images that may be used to identify the location (e.g., coordinates) of the patient target region centroid. Since the target sensor is a "null" or constant-value sensor, the sensor data reading throughout the treatment session represents the location of the patient target region centroid as initially identified during the patient localization phase of the treatment session. Since the sensor data reading (and thus the initial location of the centroid) may be the origin of the static frame (which is also the same reference frame as the radiation therapy system), the image of this constant-value sensor reading may be a delta function that is centered at the origin. This collapses the fluence map calculation such that the firing filter is convolved with an "identity" delta function $\delta_{identity}$:

$$f_i = p_i * \delta_{identity} = p_i$$

The fluence map delivered at firing position i is simply the firing filter $p_i$ for that firing position. That is, during a treatment session, as long as the patient is positioned such that the tumor centroid location at the time of treatment matches the tumor centroid location during treatment planning, a fixed, pre-calculated fluence map may be delivered to the tumor without additional target sensor data. Although this form of treatment delivery may be similar to standard IMRT/SBRT radiation delivery, but because the treatment planning was performed in the tumor POV frame instead of the static frame, the radiation delivered to the patient may be reduced as compared to standard IMRT/SBRT methods, while still meeting the same dose goals and objectives. Standard IMRT/SBRT methods perform treatment planning based on ITV boundaries defined in the static frame, which may encompass a larger region or volume than a sensor characterization PDF. The fluence maps and/or firing filters optimized based on the comparatively larger ITV may result in higher levels of irradiation to surrounding healthy tissue than when fluence maps and/or firing filters are optimized based on the sensor characterization PDF.

While the examples above describe a constant-value target sensor as target sensor systems that include a CT imaging system and a PET imaging system, it should be understood that in other variations, target sensor systems may include one or more of any of the imaging systems previously described herein, alone or in combination with each other. For example, instead of a CT imaging system that may be used in conjunction with a PET imaging system, a target sensor system may include a MR imaging system, alone or in conjunction with a CT imaging system. In some variations, the constant-value sensor may be a position sensor (such as any of the position sensors described above).

Method (1000) may also be used in a non-therapeutic manner, for example, in a QA session where the patient is replaced with a phantom and/or fluence measurement device. Optionally, the phantom and/or fluence measurement device may be mounted on a motion stage, which may be a mechanical apparatus configured to move the phantom and/or fluence measurement device according to motion trajectories that simulate patient and/or patient target region motion. The motion may be based, in some variations, on a motion dwell histogram for the target region. The phantom(s) and/or fluence measurement device(s) may be set up with target sensors and/or target sensor system as described above with a patient. As applied to a non-therapeutic radiation delivery session (e.g., a QA session), method (1000) may comprise defining (1002) the location of centroid of a target region (e.g., a phantom target region) using target sensor data acquired during the QA session, generating (1004) an image based on the acquired target sensor data acquired, calculating (1006) a radiation fluence map for delivery by convolving the generated image with a firing filter, and delivering (708) radiation according to the calculated radiation fluence map to a target region (e.g., a phantom target region).

Figure 11A:
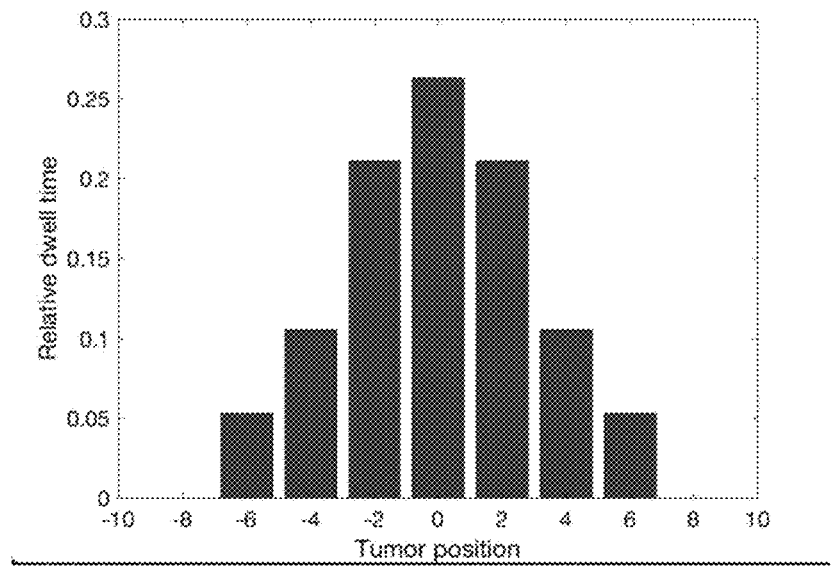
FIGS. 11A-11C depict simulation results of one example of radiotherapy treatment planning and radiation delivery methods.
Figure 11B:
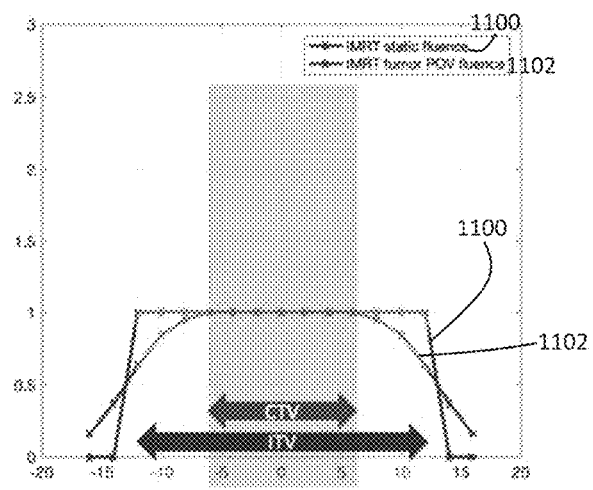
Figure 11C:
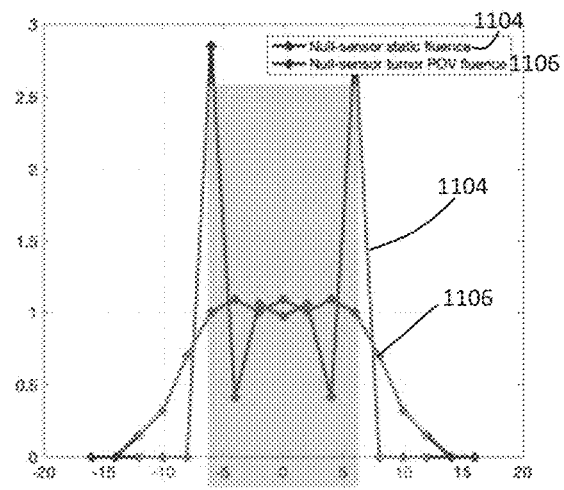

FIGS. 11A-11C depict simulation results of one example of radiotherapy treatment planning and delivery to a 12 mm long patient target region (e.g., a clinical target volume or CTV) that is moving linearly (1-D) with a ±6 mm. FIG. 11A depicts the motion dwell histogram for the patient target region. In traditional treatment planning methods for IMRT/SBRT, based on this motion profile, an ITV may be defined in the static frame having a size of 24 mm (12 mm tumor length+6 mm displacement in one direction+6 mm displacement in the other direction). The fluence delivered based on standard ITV-based treatment planning methods may have the profile depicted in the plot of FIG. 11B. Trace (1100) represents the delivered fluence in the static frame and trace (1102) represents the delivered fluence in the tumor POV frame. Although the delivered fluence in the tumor POV frame is somewhat blurred as compared to the delivered fluence in the static frame, it still covers the entire extent of the 12 mm patient target region (or CTV). FIG. 11C depicts the profile of the fluence delivered based on the treatment planning methods disclosed herein (i.e., based on sensor characterization PDFs in the tumor POV frame); that is, based on the constant-value target sensor planning and delivery methods described in FIGS. 9 and 10. Trace (1104) represents the delivered fluence in the static frame and trace (1106) represents the delivered fluence in the tumor POV frame. Although the delivered fluence in the static frame has fluence peaks at the edge of the patient target region (or CTV), giving it an overall irregular horn-shaped profile, it still covers the entire extent of the 12 mm patient target region (or CTV). While both methods deliver the prescribed dose to the entire patient target region, the difference between the fluence profile of FIG. 11B and FIG. 11C is that by treatment planning in the tumor POV frame using the methods described herein, there is an overall 35% reduction of radiation exposure to the patient.

The invention claimed is:

1. A radiotherapy system comprising:
   a patient platform;
   a therapeutic radiation source movable to one or more firing positions about the patient platform;
   a target sensor system comprising a target sensor that acquires sensor data; and
   a controller in communication with the therapeutic radiation source and the target sensor system, wherein the controller is configured to calculate a radiation fluence map for delivery to a target region by convolving an image generated from sensor data with a shift-invariant firing filter derived from a sensor characterization probability density function (PDF) of the target sensor, and wherein the controller is configured to deliver radiation according to the calculated radiation fluence map.

2. The system of claim 1, wherein the target sensor is a first target sensor and the target sensor system comprises a second target sensor.

3. The system of claim 2, wherein at least one of the first target sensor and the second target sensor is a position sensor configured to be coupled to a patient disposed on the patient platform.

4. The system of claim 3, wherein the position sensor is configured to be coupled to a target region.

5. The system of claim 3, wherein the position sensor comprises an X-ray source and X-ray detector disposed across from the X-ray source configured to detect a position of an implantable fiducial.

6. The system of claim 3, wherein the position sensor comprises an optical imaging system configured to track an optical fiducial that is attached to a patient's skin, and wherein the target sensor system further comprises an optical camera configured to detect a position of the optical fiducial.

7. The system of claim 2, wherein the controller is configured to receive a first sensor data reading from the first target sensor and a second sensor data reading from the second target sensor, wherein the shift-invariant firing filter is a first shift-invariant firing filter for the first target sensor, and the sensor characterization PDF is a first sensor characterization PDF for the first target sensor, and wherein the controller is further configured to calculate the fluence map for delivery by summing (a) the convolution of the first sensor data image with the first shift-invariant firing filter, and (b) a convolution of a second image generated from the second sensor data with a second shift-invariant firing filter derived from a second sensor characterization PDF of the second target sensor.

8. The system of claim 7, wherein the first target sensor is a first type of sensor and the second target sensor is a second type of sensor that is different from the first type.

9. The system of claim 8, wherein the second target sensor is a position sensor.

10. The system of claim 8, wherein the first target sensor is a positron annihilation emission path sensor and the second target sensor is a target region position sensor.

11. The system of claim 8, wherein the first target sensor is an image sensor and the second target sensor is a position sensor.

12. The system of claim 8, wherein the first target sensor comprises at least one of a 3-D PET sensor, 2-D X-ray sensor, projection image sensor, fluoroscopy image sensor, CT image sensor, and MR sensor, and the second target sensor comprises a position sensor.

13. The system of claim 1, wherein the sensor characterization PDF is a sensor error characterization PDF that represents a rate of sensor data errors.

14. The system of claim 1, wherein the sensor characterization PDF represents a rate of sensor data variability.

15. The system of claim 1, wherein the sensor characterization PDF comprises one or more of: a 1-D plot of sensor data, a 2-D plot of sensor data, and/or a 3-D plot of sensor data, and a histogram representing sensor data variability.

16. The system of claim 3, wherein the image generated from the position sensor data is a delta function, a gaussian function, and/or a truncated gaussian function that is centered at a location that corresponds to the position sensor data.

17. The system of claim 1, wherein the target sensor comprises one or more image sensors, the sensor data comprises imaging data, and the sensor characterization PDF of the target sensor comprises an image.

18. The system of claim 17, wherein the one or more image sensors comprise an image sensor selected from the group consisting of PET sensors, MRI sensors, and CT sensors.

19. A method for radiation delivery, the method comprising:
acquiring a sensor data reading from a target sensor;
generating a sensor image from the sensor data reading;
calculating a radiation fluence map for delivery to a target region by convolving the sensor image with a shift-invariant firing filter derived from a sensor characterization probability density function (PDF) of the target sensor; and
delivering radiation according to the calculated radiation fluence map to the target region.

20. The method of claim 19, wherein the sensor characterization PDF is a sensor error characterization PDF that represents a rate of sensor data errors.

21. The method of claim 19, wherein the sensor characterization PDF represents a rate of sensor data variability.

22. The method of claim 21, wherein the sensor characterization PDF comprises one or more of: a 1-D plot of sensor data, a 2-D plot of sensor data, and/or a 3-D plot of sensor data, and a histogram representing sensor data variability.

23. The method of claim 19, wherein the target sensor is a position sensor.

24. The method of claim 23, wherein the sensor image is a delta function, a gaussian function, and/or a truncated gaussian function that is centered at a location that corresponds to the position sensor data reading.

25. The method of claim 24, wherein the position sensor comprises a target region position sensor.

26. The method of claim 24, wherein the position sensor comprises an X-ray projector system that is configured to track an implantable fiducial.

27. The method of claim 24, wherein further comprising attaching an optical fiducial to a patient's skin and tracking the optical fiducial using an optical imaging system.

28. The method of claim 19, wherein the target sensor is a null position sensor where the sensor data reading is a constant position value that represents a centroid of the target region, and the sensor characterization PDF of the null position sensor comprises a plurality of position values that represent a location of the centroid of the target region over time.

29. The method of claim 28, wherein the sensor image is a delta function, a gaussian function, and/or a truncated gaussian function that is centered at a location that corresponds to the position sensor data reading.

30. The method of claim 28, wherein the sensor characterization PDF comprises a motion dwell histogram of the target region.

31. The method of claim 28, wherein the plurality of position values is determined using 4-D CT imaging data.

32. The method of claim 19, wherein the shift-invariant firing filter corresponds to a firing position of a therapeutic radiation source and calculating the fluence for delivery comprises calculating a fluence for delivery at the firing position by convolving a projection of the sensor image on the firing position with the shift-invariant firing filter for the firing position.

33. The method of claim 19, wherein the target sensor comprises one or more image sensors, the sensor data reading comprises imaging data, and the sensor characterization PDF of the target sensor comprises an image generated from the imaging data.

34. The method of claim 33, wherein the one or more image sensors comprise an image sensor selected from the group consisting of PET sensors, MRI sensors, and CT sensors.

35. The method of claim 19, wherein the target sensor is a first target sensor, the sensor data reading is a first sensor data reading, the image is a first sensor data image, the shift-invariant firing filter is a first shift-invariant firing filter, and the sensor characterization PDF is a first sensor characterization PDF, and wherein the method further comprises:
  acquiring a second sensor data reading from a second target sensor;
  generating a second sensor data image from the second sensor data reading; and
  wherein calculating the fluence map for delivery comprises summing (a) the convolution of the first sensor data image with the first shift-invariant firing filter, and (b) a convolution of the second sensor data image with a second shift-invariant firing filter derived from a second sensor characterization PDF of the second target sensor.

36. The method of claim 35, wherein the first target sensor data reading contains a first type of data and the second target sensor data reading contains a second type of data that is different from the first type of data.

37. The method of claim 36, wherein the second target sensor is a position sensor.

38. The method of claim 36, wherein the first target sensor data reading comprises positron annihilation emission path data and the second target sensor data reading comprises target region location data.

39. The method of claim 36, wherein the first target sensor data reading comprises partial imaging data and the second target sensor data reading comprises target region location data.

40. The method of claim 36, wherein the first target sensor data reading comprises at least one of 3-D PET imaging data, 2-D X-ray imaging data, projection imaging data, fluoroscopy imaging data, CT imaging data, and MR imaging data, and the second target sensor data reading comprises target region location data.

41. The method of claim 35, wherein the second sensor characterization PDF is a sensor error characterization PDF.

42. The method of claim 19, wherein the shift-invariant firing filter corresponds to a firing position of a therapeutic radiation source and calculating the fluence for delivery comprises calculating a fluence for delivery at the firing position by projecting the sensor data reading on the firing position, generating a second sensor image of the projected sensor data reading, and convolving the second sensor image with the shift-invariant firing filter for the firing position.

* * * * *